United States Patent [19]
Dasgupta et al.

[11] Patent Number: 6,086,736
[45] Date of Patent: Jul. 11, 2000

[54] ELECTROMIGRATION INJECTION FROM A MICRORESERVOIR-ELECTRODE IN CAPILLARY SEPARATION SYSTEMS

[75] Inventors: Purnendu K. Dasgupta, Lubbock, Tex.; Kazimierz Surowiec, Lublin, Poland

[73] Assignee: Texas Tech University, Lubbock, Tex.

[21] Appl. No.: 09/043,797

[22] PCT Filed: Aug. 1, 1997

[86] PCT No.: PCT/US97/13663

§ 371 Date: Mar. 30, 1998

§ 102(e) Date: Mar. 30, 1998

[87] PCT Pub. No.: WO98/05950

PCT Pub. Date: Feb. 12, 1998

Related U.S. Application Data

[60] Provisional application No. 60/023,074, Aug. 2, 1996.

[51] Int. Cl.[7] .......................... G01N 27/26; G01N 27/447
[52] U.S. Cl. ............................ 204/453; 204/604
[58] Field of Search .................... 204/451, 452, 204/453, 454, 455, 601, 602, 603, 604, 605

[56] References Cited

U.S. PATENT DOCUMENTS 5,814,199  9/1998  Dasgupta ................... 204/453

OTHER PUBLICATIONS

Mårten Jansson et al, "Micro vials or a silicon wafer for sample introduction in capillary electrophoresis" Journal of Chromatography vol. 626 pp. 310–314, 1992. No month available.

Chuzo Fujimoto, "Charged Polyacrylamide Gels for Capillary Electro Chromatographic Separations of Uncharged, Low Molecular Weight Compounds" Analytical Chemistry, vol. 67, No. 13, pp. 2050–2053, Jul. 1, 1995.

Hong–Feng Ying et al, "A Miniature Device for Electrokinetic or Hydrodynamic Sample Introduction from Small Volumes in Capillary Electrophoresis" Journal of High Resolution Chromatography, vol. 14 pp. 282–284, Apr. 1991.

*Primary Examiner*—Jill Warden
*Assistant Examiner*—John S. Starsiak, Jr.
*Attorney, Agent, or Firm*—Flehr Hohbach Test Albritton & Herbert LLP

[57] ABSTRACT

A capillary electrophoresis system (10) comprising: a separation capillary (20) with a first distal tip (30) and a second distal tip (140); a source vessel (50) containing a solution (40); a microreservoir-electrode (59) comprising a wire loop; a power source (60) connected to the microreservoir-electrode by wire (57); a control system (200); a detector (90); and a final destination vessel (160) containing electrolyte (150) and a ground electrode (155).

13 Claims, 14 Drawing Sheets

ELECTROMIGRATION INJECTION FROM A MICRORESERVOIR-ELECTRODE IN CAPILLARY SEPARATION SYSTEMS

RELATIONSHIP TO OTHER PATENT APPLICATIONS

This application is the national stage of International application No. PCT/US97/13663, which claims the benefit of U.S. provisional patent application Ser. No. 60/023,074, filed on Aug. 2, 1996 and entitled ELECTROMIGRATION INJECTION FROM A SMALL LOOP IN CAPILLARY ELECTROPHORESIS.

BACKGROUND OF THE INVENTION

Capillary electrophoresis ("CE") and associated capillary scale technologies provide very important analytic techniques for separation and quantitation of large biomolecules. Although such techniques are useful in separating and detecting small ions, ion chromatography has been a more dominant technique. The more successful ion chromatography detection techniques have recently been found to be applicable to capillary electrophoresis. One result has been so-called suppressed conductometric capillary electrophoresis separation systems ("SuCCESS"). SuCCESS technology can produce low $\mu$g/L limits of detection for a variety of small ions in a robust manner without special efforts towards pre-concentration. (See U.S. Pat. Nos. 5,358,612 and 5,433,838 to Dasgupta and Bao.)

However, capillary electrophoresis is most commonly carried out using UV-Vis absorptiometric detection, as shown in FIG. 1. (See for example, "Capillary Electrophoresis" by S. F. Y. Li, Elsevier, N.Y. 1992. As shown in FIG. 1, a CE analysis system 10 includes a separation capillary 20 whose distal tip 30 initially is in fluid communication with a solution 40 containing analyte samples A, and typically also containing other substances X. Solution 40 is retained in a source vessel 50 and is electrically coupled by an electrode 55 by a wire 57 to a power source 60 that is at a high voltage ("HV") potential V1, typically many kilovolts. A second or ground electrode 155 is often disposed in a final destination vessel 160. As shown in FIG. 1, capillary 20 passes through a UV-visible absorption detector 90 before reaching final destination vessel 160.

Coupling HV power supply 60 to capillary 20 as shown in FIG. 1 results in a left-to-right direction migration of analyte A within the capillary, as indicated by the rightward-pointing arrows. Such migration can commence within seconds of energizing power supply 60. Power supply 60 may then be turned-off, after which tip 30 of capillary 20 may be relocated into a second vessel 70 containing running electrolyte 80. Power supply 60 is coupled to solution 80 via an electrode 55, which may be identical to (or indeed the same as) electrode 55 described in conjunction with vessel 50. Power source 60 may then be re-energized, which continues the downstream migration of the sample analyte. This type of electric field induced analyte injection is termed electromigrative or electrokinetic injection ("EI").

The distal end of capillary 140 is in fluid communication with electrolyte 150 contained in a terminating electrolyte reservoir 150. Preferably electrolyte 150 is the same as running electrolyte 80, and in the embodiment shown is at ground potential.

As noted, during EI, HV is applied with the background electrolyte (BGE)-filled capillary dipped in a sample vial. In a typical situation, electroosmotic and electrophoretic movements act together to introduce the desired class of analyte ion(s) into the capillary. In general, when the electroosmotic mobility ($\mu_{eo}$) is small relative to the electrophoretic mobility ($\mu_{ep}$), conditions are most favorable for electromigrative preconcentration. Under these conditions a significant amount of analyte can be introduced without the concomitant introduction of a significant liquid volume. EI has been widely used for the trace analysis. This is especially valuable with UV-Vis detection because on-column UV-Vis absorption detectors, e.g., detector 90, typically used in CE provide relatively poor concentration detection limits. In the determination of small ions, where indirect detection is typically used, the situation is even less favorable than with direct detection.

In EI, when the sample ionic strength is very low, best results are obtained if a low mobility ion is deliberately added to the sample at a concentration that is high relative to the total concentration of the analyte. By "low mobility" what is meant is an ion having mobility lower than any of the analyte ions of interest. In such case, the added ion behaves like a terminating electrolyte and electromigrative preconcentration closely resembles isotachophoresis. In some situations, a high mobility ion is the analyte of interest and low mobility ions are already present in abundance, such as in the determination of residual sulfate in sulfonate dyes. There is no need to add any terminating electrolytes in such cases. In cases where the analyte of interest is present at a low concentration in a sample that has a significant ionic strength, it is impractical to add sufficient terminating electrolyte to make the latter the dominant current carrier.

Unfortunately, even under identical sample analyte concentrations and instrumental settings, the amount of an analyte introduced into an EI system is a strong function of sample conductance. This relationship occurs because conductance affects the rate of electroosmotic introduction. Less directly conductance also affects the rate of the electrophoretic movement through a change in the field strength experienced by the sample. Further, EI is dependent on the mobility of the analyte itself, creating a bias in favor of the high mobility ions. By "bias" it is meant that the injected sample differs from the original sample. The difference occurs because there is a relative deficit of slower moving ions, and a relative excess of faster moving ions in the aliquot injected portion as contrasted to what was originally present in the sample. Although researchers such as Lee and Yeung, Anal. Chem. 1992, 64, 1226–1231, have advanced a simple approach to improve precision of the results obtained in EI through monitoring system current, the Lee-Yeung technique does little to solve the problem caused by biased injection.

Other attempts have been made in the prior art to address the above-noted bias dependency of sample conductivity. For example, the use of two separate internal standards that bracket the entire range of analyte mobilities of interest has been suggested, as has been the standard addition of every analyte of interest. These approaches are unsatisfactory and indeed can be tedious.

Finally, the prior art has tended to overlook the fundamental fact that the EI of sample ions into a capillary is ultimately dependent upon the local electrical field. Any changes in the geometry and or the physical distance between the HV electrode and the capillary tip can profoundly affect EI. Unfortunately, it has been difficult in the prior art to reliably produce a truly symmetrical electric field.

In the prior art, the total amount of analytes in the sample aliquot from which analyte ions are EI-introduced into the capillary is very large relative to the amount of analytes actually introduced. If one could perform EI from a truly small sample volume for a long enough period, it would be possible, in principle, to introduce virtually all the analyte ions of interest into the capillary in an exhaustive manner. The sample volume would not become deionized or become non-conductive in the process. Deionization or conductivity loss would not occur because electro-generated $H^+$ or $OH^-$, and the appropriate counter-ion already present in the sample, and those migrating against the EOF into the sample from the capillary, would maintain the sample conductive. Indeed, if EI could be carried out long enough, significant amounts of $H^+$ or $OH^-$ would be introduced. Unfortunately exhaustive electromigration cannot be effectively practiced in the prior art.

Thus, there is a need for an easily produced microreservoir, preferably having a sub-$\mu$L liquid capacity, that can be used in exhaustive electromigration and electrophoresis. Preferably such microreservoir should permit the entire sample within to be readily subjected to a symmetrical electric field. Further, the microreservoir should permit the entry tip of a separation capillary to be disposed at the symmetrical center of the sample. A system incorporating these features and methodology would advantageously reduce the effects of conductivity in electromigration injection capillary electrophoresis.

The present invention provides such a method and apparatus.

SUMMARY OF THE INVENTION

Undesired bias effects are reduced in a separation system using electromigration injection ("EI") by exhaustively introducing analyte ions of a desired polarity in the sample into the separation capillary using a microreservoir-electrode. (The separation system may be an electrophoretic or sn electrochromatographic system.) A wire loop or hemisphere formed in a metallized base defines a microreservoir of finite volume that preferably is symmetrical to reduce the time required to achieve exhaustion. The entry tip of the separation capillary is preferably disposed at the center of the microreservoir, which advantageously reduces the time required to achieve exhaustion.

Because the microreservoir is an electrical conductor, it is coupled to one terminal of the high voltage power source and constitutes one of the high voltage electrodes in the separation system. With high voltage applied, the sample under analysis is subjected to an electric field within the microreservoir, and the separation system is used to conduct an exhaustive injection of the analyte. Advantageously, conducting exhaustive electro-injection in the separation system substantially reduces bias effects resulting from faster moving ions in the sample entering the capillary sooner than slower moving ions of the same polarity. Exhaustive injection using electromigration results in essentially quantitative sample injection. This injection occurs substantially independently of the conductivity of the sample, and substantially independently of the ionic mobility of the various analyte ions of the same polarity.

Exhaustive electroinjection is preferably carried out as follows. Using a preferably symmetrical microreservoir-electrode whose volume is reproducible and small, e.g., <2 $\mu$L, a small aliquot or portion is taken. The portion may be a film that is formed by dipping and withdrawing a loop microreservoir-electrode into and out of a vessel containing the sample. Using the microreservoir-electrode as one electrode, EI potential is applied for a desired period, e.g., 30 seconds to 60 seconds, during which time all ions of the desired polarity present in the sample are essentially quantitatively injected into the tip of the separation capillary. At first the faster moving ions are injected and as these ions are depleted, slower moving ions are injected into the capillary. This result is attained because the reservoir volume is relatively small. The result is that bias effects are reduced in that the injected sample will contain a truer representation of the more slowly moving ions, in addition to the faster moving ions.

Other features and advantages of the invention will appear from the following description in which the preferred embodiments have been set forth in detail, in conjunction with the accompanying drawings.

DETAILED DESCRIPTION OF THE PREFERRED EMBODIMENTS

Figure 1:
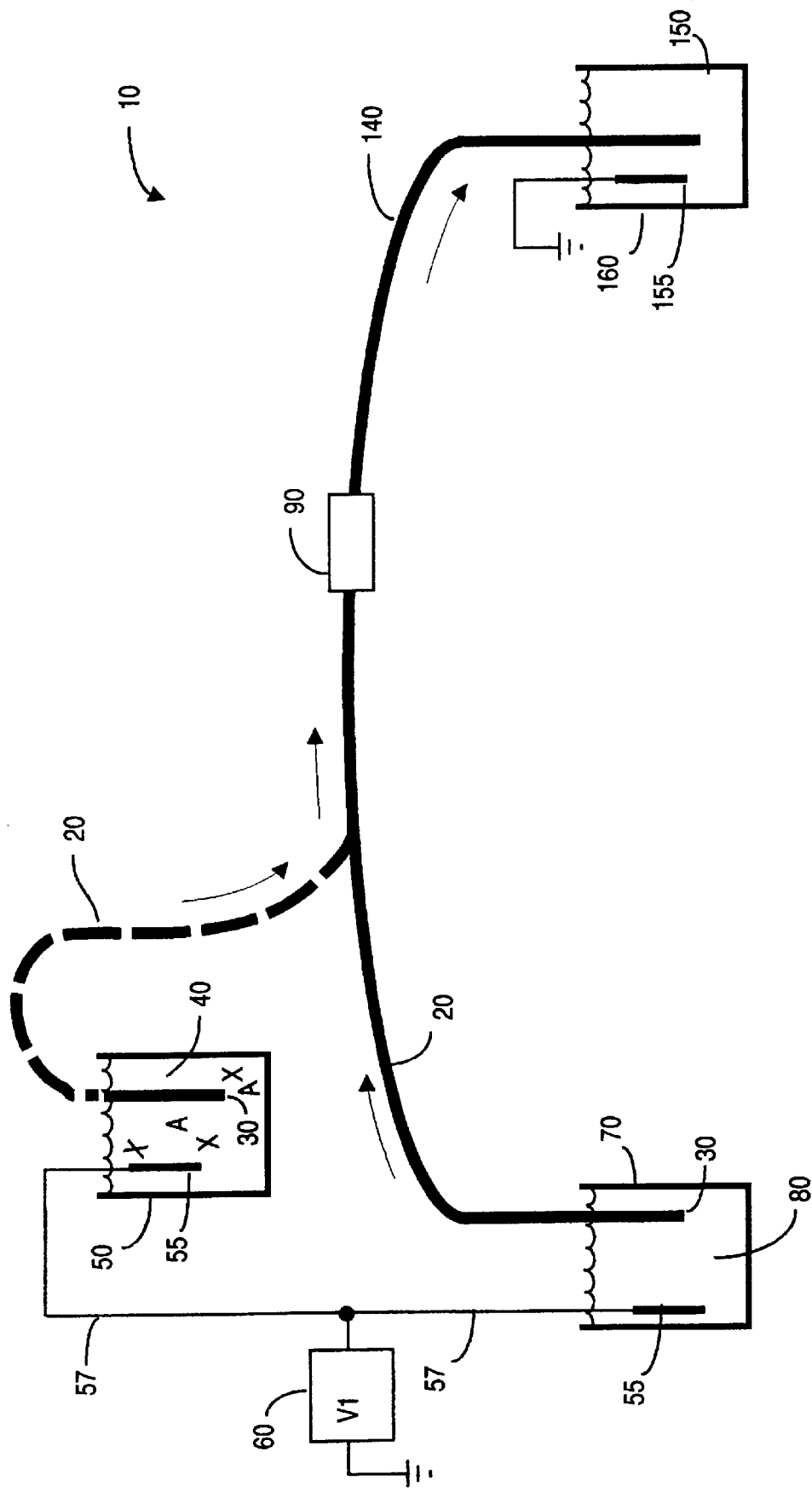
FIG. 1 depicts a conventional separation system, according to the prior art.
Figure 2:
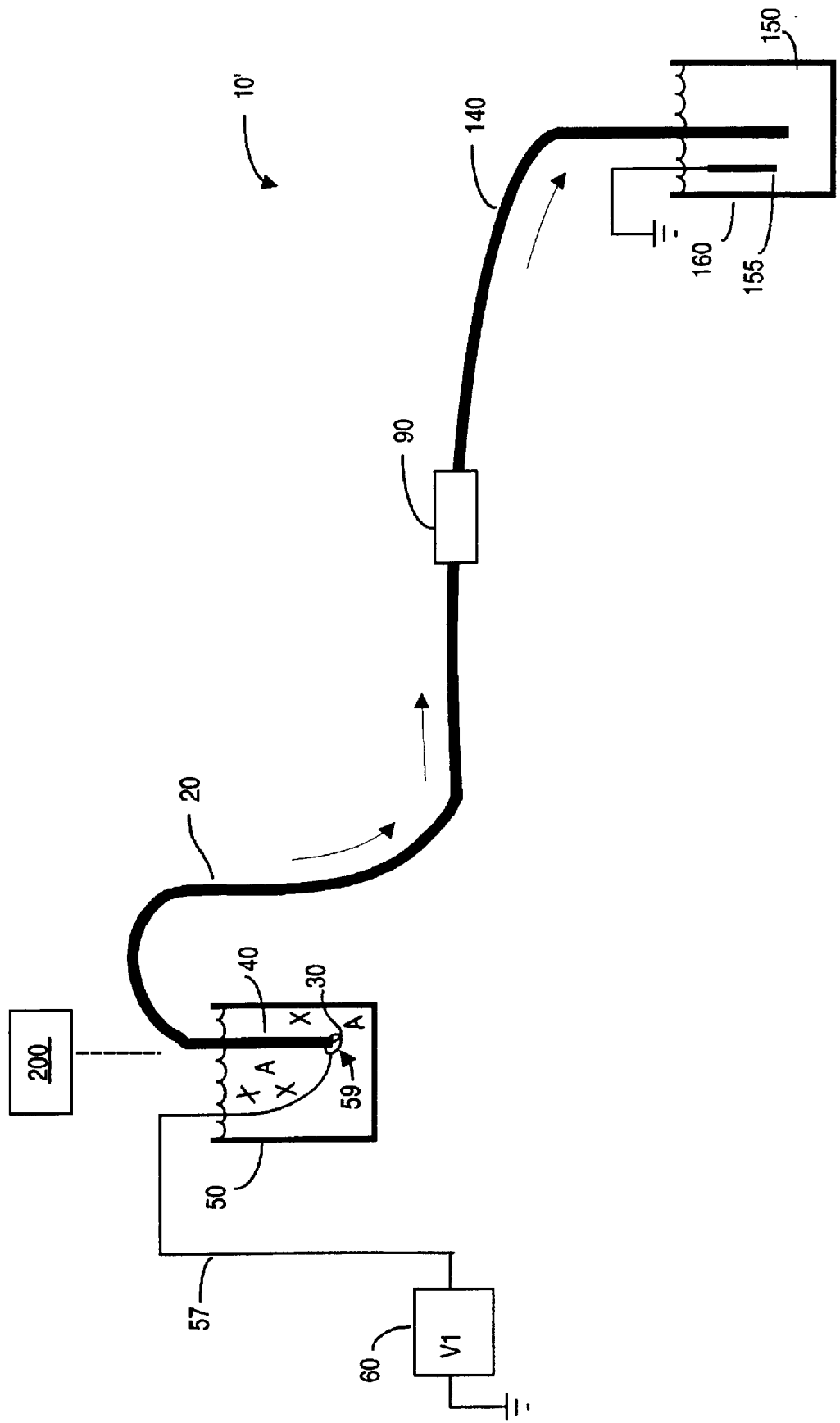
FIG. 2 depicts an EI separation system, according to the present invention.

FIG. 2 shows a somewhat modified CE system 10' in which a microreservoir-electrode 59 is provided. As will be described herein, a microreservoir-electrode preferably defines a volume holding capacity of approximately 1 $\mu$L or less and advantageously serves as an electrode, in lieu of electrode 55 in prior art FIG. 1. The microreservoir-electrode geometry is symmetrical, preferably a loop formed from conductive wire (see FIGS. 3A, 3B) or a hemisphere defined in a metal or conductive base (see FIG. 3C).

System 10' was used by applicants as a fully automated custom designed CE system that used fused silica capillaries 20 having 74 $\mu$m inner diameter, 360 $\mu$m outer diameter, and 60 cm lengths. Such capillaries are available from Polymicro Technologies, Phoenix, Ariz. The high voltage ("HV") power source 60 was provided by a programmable HV power supply, model CZE 2000, available from Spellman High Voltage, Plainview, N.Y. A variable wavelength UV-Vis on-column absorbance detector 120 or 130 was used (a LINEAR model 206 PHD available from Thermo Separation Systems) in combination with UV-206 data acquisition software (LINEAR) operating on a 80386 class personal computer (PC) (not shown). Of course other equipment and other sized capillaries might be used. Those skilled in the art will appreciate that system 10' may in fact comprise a capillary electrochromatography system. In such case, capillary 20 would be a packed column rather than a hollow tube.

An automated system that precisely controls withdrawal of the capillary sampling head from the sample is especially important in practicing the present invention. It is desired to withdraw a reproducible amount of liquid from vessel 50 as a film on a wire loop, such as microreservoir-electrode loop 59 shown in FIGS. 3A and 3B. A slow rate of withdrawal is needed to ensure a reproducible amount of liquid retained in the film. In applicants' experiments, system automation was accomplished by using a modified fraction collector (model 2110, BIO-RAD, Richmond, Calif.) as an autosampler. A number of pneumatic linear actuators, governed by electrically operated air solenoid valves, served to provide horizontal and vertical motion to the capillary head. System operation was controlled by a programmable microcontroller (a Micro Master LS unit available from Minarik Electric, Los Angeles, Calif.). It is understood that other control systems may instead be employed. Collectively, these components and sub-systems are shown generically in FIG. 2 as 200. Physical movement of microreservoir-electrode 59 is not shown to avoid cluttering FIG. 2.

Figure 3A:
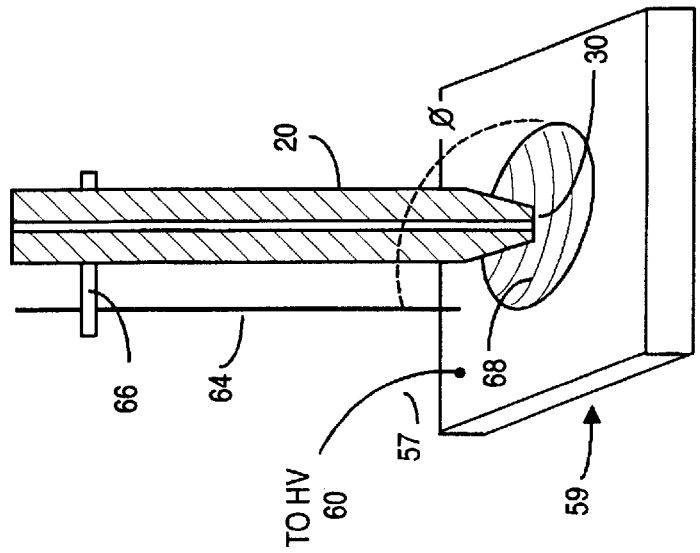
FIG. 3A depicts a first embodiment of a microreservoir-electrode using inclined loop geometry and an associated support wire, according to the present invention.
Figure 3B:
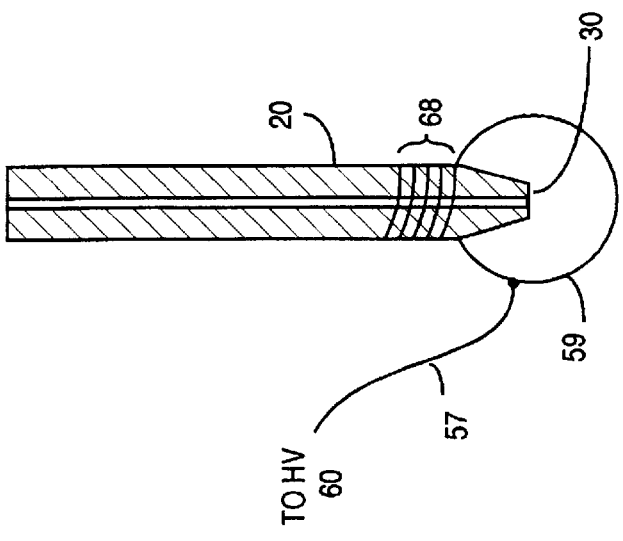
FIG. 3B depicts a second embodiment of a microreservoir-electrode using planar loop geometry in which the capillary longitudinal axis and loop radius are on a common plane, according to the present invention.

Applicants' publication in *Anal. Chem.* 1996, 68, 1164–1168 disclosed general techniques to form wire loops at the tip of a capillary. By contrast, the loops used in the embodiments of the present invention shown in FIG. 3A and 3B are substantially larger and are therefore fairly simple to fabricate. Briefly, 5/64 inch to 1/8 inch diameter loops were initially made by wrapping 135 $\mu$m diameter stainless steel wire around suitably sized drill bits and were held with one or two twists.

The wire loop embodiment microreservoir-electrodes (abbreviated "loop") were used in two different geometries, shown in FIGS. 3A and 3B. In FIG. 3A, the plane of loop 59 is inclined at an angle $\phi$ of 45° to 90° relative to the longitudinal axis of the separation capillary 20. A vertical support wire 64, parallel to capillary 20, holds loop 59 in position. Note that the loop is symmetrical, and that the center of tip 30 is disposed symmetrically at the center of the loop. The support wire and the capillary were retained a few cm above the lower capillary tip 30 by a small Plexiglas jig, depicted as 66. A conductive wire 57 couples the wire loop to the HV power supply 50, such that loop 59 forms one electrode in the separation system 10'. An advantage of using a loop microreservoir-electrode is that a very symmetrical electric field is produced across the electrode. In the embodiment of FIG. 3A, upon withdrawal from a liquid, the amount of liquid held in the loop decreases as the loop plane angle becomes more vertical.

In the embodiment of FIG. 3B, loop 59 is formed around the capillary tip 30, the capillary axis now being parallel to the plane of the loop. The terminal wire 68 is wrapped around the tip of the capillary and is affixed thereto by epoxy adhesive.

In the embodiments of FIGS. 3A and 3B, high voltage connections were made to the protruding wire (or support wire) 64 or to a wire 57 coupled to the loop. As noted, the result is that loop 59 serves as a HV electrode, in lieu of electrode 55 in FIG. 1. Because the present experiments were limited to reversed polarity (–HV), stainless steel material was adequate to fabricate loop electrodes 59.

Figure 3C:
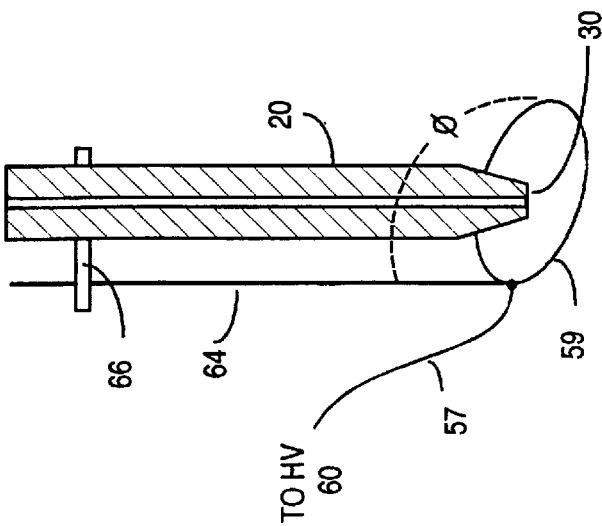
FIG. 3C depicts a third embodiment of a microreservoir-electrode comprising a hemisphere formed in a conductive base material, according to the present invention.

As noted, it is desired that microreservoir-electrode 59 retain a finite amount of liquid, e.g., <1 $\mu$L, and provide a uniform electric field across the microreservoir when used in system 10'. A symmetrical loop such as shown in FIGS. 3A and 3B meet these goals. In the embodiment of FIG. 3C, microreservoir-electrode 59 comprises a base of electrically conductive material, e.g., metal, having a surface in which a hemisphere depression 68 is formed. Although the base is shown as square, for ease of illustration, a circular base could instead be used, and would further contribute to symmetry. The hemisphere depression is sized to retain a desired amount of liquid, e.g., <1 $\mu$L, thus serving as a microreservoir of finite volume capacity. For retaining a fixed volume, such a reservoir may also be made to be self-siphoning. Because the microreservoir is made of an electrically conductive material, wire 57 may be connected to the base of microreservoir-electrode 59, permitting it to also function as an electrode. Again, the tip 30 of capillary 20 is disposed symmetrically at the center of the microreservoir hemisphere 68. The overall result is that a sample retained in hemisphere 68 is subjected to a symmetrical electric field.

With respect to reagents used with system 10', all solutions were prepared in distilled deionized water (e.g., Barnstead Nanopure) having specific resistance greater than 16 M$\Omega$·cm. Sodium chromate (5 mM) was made fresh daily from a 50 mM stock prepared from $Na_2CrO_4 \cdot 4H_2O$, A. R. Grade, Mallinckrodt, adjusted to pH 8.0 with 0.1 M $H_2SO_4$. Cetyltrimethylammonium hydroxide (CTAOH) was prepared by ion exchanging a cetyltrimethylammonium chloride solution through an $OH^-$-form 200–400 mesh Dowex 1×8 anion exchange column, and used from a 20 mM stock. CTAOH was used as the electroosmotic flow ("EOF") modifier (to achieve flow to the ground electrode with –HV applied) and was added to the chromate electrolyte to attain a final concentration of 0.5 mM.

In operating system 10', capillary 20 was first filled with the BGE and then tip 30 was lowered into and withdrawn from one sample vial for washing loop 59. The capillary then entered a second identical sample vial and was slowly withdrawn to form a sample film on the loop. The capillary was next moved horizontally and lowered into a position at a level equal to the liquid level on the destination side, e.g., vessel 160 in FIG. 2. In this position, the region around the loop is cylindrically enclosed and a small flow of $N_2$ ($\approx$20–25 cm$^3$/min) serves to prevent excessive intrusion of $CO_2$. Electromigration voltage (−3 kV, except as stated) was then applied from HV source 60. As noted, microreservoir 59 served as one electrode in system 10', the other electrode being coupled to electrode 155 (or to some other location in system 10').

After a desired EI time period, the capillary is put into a first BGE vial for washing and is then lowered into a second, fresh, BGE vial for operation. An operating voltage of −18 kV was used for electrophoresis. Essentially the same procedure was used in an analogous manner when EI was carried out from a conventional sample vial. The determination of anions was studied and except as described, the sample constituted a mixture of chloride (200 μg/L), nitrate (400 μg/L), formate (400 μg/L) and acetate (400 μg/L), all as sodium salts.

Consider now the underlying principles at work when practicing the present invention. In EI, the quantity $Q_i$ of species i introduced during time t into a capillary of length L and inner radius $r_C$, across which a voltage V is applied is given by:

$$Q_i=(\mu_i+\mu_{eo})\pi r_C^2 VC_i t/L \quad (1)$$

where $\mu^i$ and $\mu^{eo}$ are respectively electrophoretic and electroosmotic mobilities and $C_i$ is the concentration of species i. This analysis assumes that the field E at the tip of the capillary is the same as the field inside the capillary and is therefore given by V/L. The flux occurs through the capillary inlet cross section. The bulk reservoir of analyte i is so large that C' is essentially unchanged during the duration of EI. Thus, as long as the rate of migration of the analyte ion within the capillary does not influence the rate of analyte introduction at the capillary tip, a more general formulation of equation (1) will be:

$$M_i=dQ_i/dt=(E\mu_i+u_{eo})aC_i \quad (2)$$

where $M_i$ is the mass transport rate (eq/s) of ion i through any area a around the capillary tip towards the capillary where the concentration of species i is $C_i$.

In practice, the field E inside and outside the capillary is unlikely to be the same. Nevertheless, the electroosmotically introduced component of EI is governed by the EOF generated in the capillary. Therefore, the EOF governed component of EI is better specified directly, in terms of the bulk flow velocity $\mu_{eo}$ generated in the capillary. Obviously, if $\mu_{eo}$ is very small relative to $E_{\mu i}$, equation (2) simplifies to:

$$M_i=E\mu_i aC_i \quad (3)$$

Consider now the field geometry at the capillary tip, and film resistivity. As a representative simplified case, consider that the sample constitutes a thin circular disk of radius $r_{out}$ and thickness h, and that capillary tip is placed at the center of the disk. As long as h is small relative to $r_{out}$, one may assume that diffusive transport in the vertical direction is not a limiting process.

The perimeter area of the disk, $2\pi r_{out}h$, constitutes one electrode. Note that even if the film/disk were thicker than the diameter of the wire constituting the loop, the electrode area would still be correctly approximated by the entire perimeter area for a thin disk. The capillary cross section, $\pi r_C^2$, represents the second, virtual, electrode. In most cases, $r_C$ is very small compared to $r_{out}$. Thus, instead of a planar geometry, one may approximate the central electrode as having a cylindrical geometry of radius re with an area equal to the capillary cross section. Whence, $$r_e=r_C^2/2h \quad (4)$$

Thus, the result is an annular electrode system, initially having a medium of homogeneous resistivity ρ filling the annulus, where:

$$\rho=1/(\Sigma\lambda_j C_j) \quad (5)$$

in which $\lambda_j$ is the equivalent conductance (in S cm$^2$ eq$^{-1}$) of ion j, and in which $C_j$ is its concentration in equivalents/cm$^3$. This yields resistivity ρ in Ω·cm. Ions j not only include the analyte anions of interest (ions i, e.g., chloride), but also include an equal concentration of counter-ion (e.g., sodium) that is present in the medium for maintaining electroneutrality.

In this analysis, applicants have assumed that the rate limiting process of interest is the migration of ions i into the capillary. As such, the reverse migration of the counter-ion from the capillary (where it is present in very large concentration relative to concentration of the analyte ions in the film) is not the limiting step. It should also be noted that EI is accompanied by the electrolytic production of OH$^-$ at the loop electrode that is maintained at a negative potential. Not only resistivity ρ in the loop film is affected by an increasing NaOH content, but OH$^-$ is also thence introduced along with the sample ions, the relative amount increasing with increasing EI period.

Consider the effects of electrical resistance of the loop. If the inner electrode has a radius r and a thickness h, and if the second electrode is situated an infinitesimal distance dr away, the inter-electrode resistance dR is given by:

$$dR=\rho dr/2\pi rh \quad (6)$$

Whence $$R=(\rho/2\pi h)\log r \quad (7)$$

Thus, applying the above to the embodiments of interest in which there is a loop of outer radius rout and inner radius $r_C$, the resistance of the loop, $R_{loop}$ is given by:

$$R_{loop}=(\rho/2\pi h)\log(r_{out}/r_e) \quad (8)$$

Mass transfer into the capillary will now be described. In equation (3), the field E may be expressed as:

$$E=dV/dr \quad (9)$$

Current I flowing through the system is a function of total applied voltage V and the sum of the electrical resistance of the capillary ($R_{cap}$) and the resistance of the loop ($R_{loop}$). The current relationship is as follows:

$$I=V/(R_{loop}+R_{cap}) \quad (10)$$

During EI, total applied voltage remains constant during EI, and, in most practical applications, electrical resistance of the capillary ($R_{cap}$) is essentially invariant and is much greater than $R_{loop}$. current I remains essentially constant. Whence equation (9) becomes:

$$E=IdR/dr \quad (11)$$

At the tip of the capillary, area a from equation (3), through which area the mass transfer occurs, is the surface area of the inner cylindrical electrode, and is also equal to the capillary cross section. Area a may be written as:

$$A = 2\pi r_e h \quad (12)$$

Setting $r=r_C$ at the capillary tip, equation (6) then yields:

$$dR/dr = \rho/2\pi r_e h \quad (13)$$

Combining equations 3, 11, 12, and 13 yields the simple result that:

$$M_i = I\rho\mu_i C_i \quad (14)$$

A sample film is the present invention is well mixed spatially and is homogeneous. Assume that the entire film is well mixed at all times. For all the anions other than hydroxide, $$-dC_i/dt = M_i/V_f = I\rho\mu_i C_i/V_f \quad (15)$$

where $V_f$ is the volume of the loop film, given by $\pi r^2_{out} \cdot h$.

OH⁻ is also produced in the film at the rate of I/F eq/s, where F is Faraday's constant. It then follows that:

$$-dC_{OH}/dt = I(\rho\mu_{OH}C_{OH} - 1/F)/V_f \quad (16)$$

Expanding equation (5) indicates that:

$$\rho = \Sigma C_i \lambda_i + C_{OH}\lambda_{OH} + \lambda_{Na}(C_{OH} + \Sigma C_i) \quad (17)$$

Equations 15, 16, and 17 constitute a set of coupled second order differential equations for which no general solutions exist. However, the system of equations may readily be solved numerically.

Except as stated otherwise, the following system characteristics were and are assumed: loop radius 1 mm, sample volume 1 µL, sample composition Cl (200 µg/L), NO₃⁻ (400 µg/L), HCOO⁻ (400 µg/L), CH₃COO⁻ (400 µg/L), EI voltage −3 kV, capillary inner diameter 75 µm, BGE 5 mM Na₂CrO₄. For a capillary length of 60 cm, computed $R_{cap}$ is 1.008 GΩ, which is in close agreement with an observed current of −3 µA.

Computations were carried out with code written in TURBO BASIC (produced by Borland International) on a Pentium processor based PC operating at 133 MHz. Convergence of the solutions was checked by decreasing the time interval of iteration steps. Typically no significant changes were observed below an iteration step of 100 µs. All of the data described herein were based on such temporal iteration step.

It should be noted that the computing time for the above well mixed film case was not particularly demanding. But, in a more realistic environment where film composition changes radially during EI (described herein), simulating 30 s of EI with a 50 µs iteration step requires a computing time of over 14 h.

Understandably a 14 h computational time probably represents the acceptable upper time limit for PC-based computations.

Applicants' analysis was according to the following algorithm steps:

1. From the initial sample composition, compute initial value of ρ (equation 17), $R_{loop}$ (equation 8), and I (equation 10);
2. Calculate the mass (cumulative mass) of analyte ions and OH⁻ injected within the chosen iteration time interval (equation 14);
3. Calculate change in composition of the sample film, both in regard to analyte ions and NaOH (equations 15 and 16), and hence for the new composition;
4. Using the new composition, perform the same calculations as in step 1, above;
5. Cycle through steps 2, 3, and 4 until the total desired EI period has been simulated.

Figure 4:
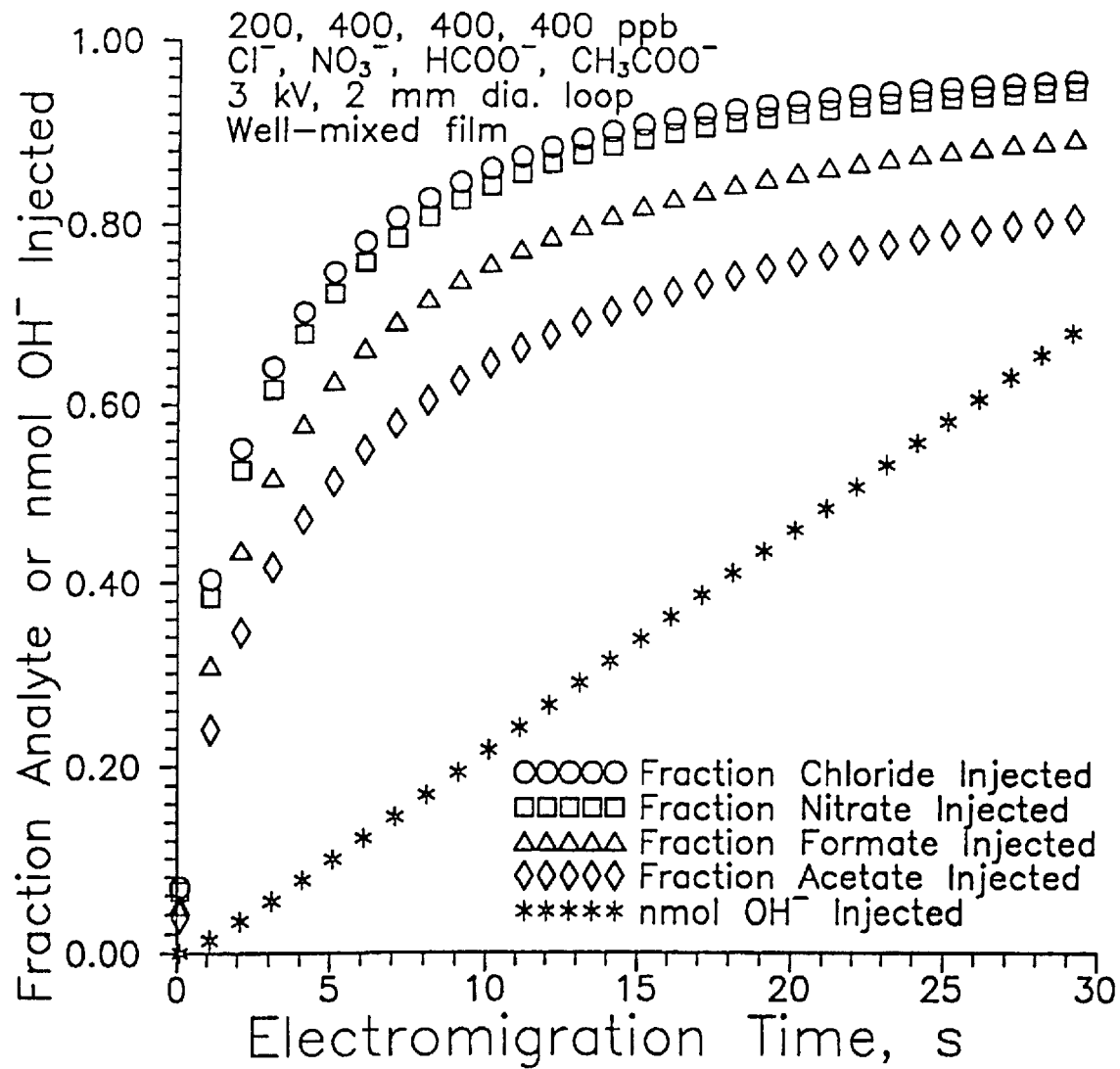
FIG. 4 depicts numerical simulation EI data from an well-mixed film, according to the present invention.

FIG. 4 shows the results of such a numerical simulation of EI for a well-mixed film. With increasing EI time, the total amount of each analyte injected approximately exponentially reaches respective limiting plateau values. However, with increasing EI time, the amount of OH⁻ injected (shown with asterisks) increases linearly. Although none of the analytes is quantitatively injected under such condition, at the end of the EI period, fast moving chloride and nitrate are nearly completely injected, 96% and 95%, respectively. However, acetate, the slowest of the four analytes, is injected to an extent of about 81%. The relative bias of chloride vs. acetate is 1.183, e.g., the extent to which the ratio of the injected amounts of chloride to acetate is greater than the ratio of the respective ions originally in the sample.

By contrast, when one computes the same relative bias for conventional EI from a sample vial from equation (1), the value obtained is the ratio of the two mobilities, 1.866. Indeed, applicants experimentally observed this as well, although data are not shown. Thus, a very significant reduction of bias can be expected if EI is carried out from a finite, limited volume, according to the present invention.

Spatial concentration gradients occur during EI. While the methodology outlined above is instructive, it is somewhat over simplifying. In reality, the loop size is finite. Further, the relatively rapid movement at different rates of ions towards the capillary entrance tend to ensure that not only the temporal composition but also the spatial composition of the film will not be constant during the EI process.

During EI, ions are depleted near the capillary entrance and must be replenished. On the other hand, in the simple model, while OH⁻ is actually produced in substantial quantity near the outer periphery of the film, it is assumed to be instantaneously mixed throughout the film, thus lowering calculated film resistance. Consequently the field across the loop and the rate of EI is also lowered, relative to what might otherwise be expected. While several levels of sophistication may be included in a model to account for these occurrences, numerical solutions are resorted to when equations pertaining to the basic model cannot be solved analytically.

The basic approach taken by applicants assumes that the film is radially divided into a number of thin segments that are individually of uniform composition. The innermost zone has a radius of RINZONE. The rest of the loop is divided outward in segments of thickness Δr, until $r_{out}$ is reached. Except as stated, simulations herein assume RINZONE to be 50 µm, which is slightly larger than the capillary inner radius of 37.5 µm. A value ΔR=10 µm is used throughout herein. For $r_{out}$=0.1 cm, there are n=96 separate zones. These n zones may be designated in terms of their radii in cm, $r_1, r_2, \ldots r_{95}, r_{96}$, where $r_1$=RINZONE, $r_2 = r_1 + 0.001$, $r_k = r_1 + (k-1) \cdot 0.001$, $r_{96} = r_{out}$, with $r_0$ designated as 0. Adopting this nomenclature, the volume $V_k$ of each zone or shell is given by:

$$V_k = \pi(r_k^2 - r_{k-1}^2)h \quad (18)$$

The electrical resistance $R_k$ of each shell is given in a manner analogous to equation (7), namely:

$$R_k = (\rho/2\pi h)\log(r_k/r_{k-1}) \quad (19)$$

with the provision that in this case $r_0$ is not zero but is the radius of the hypothetical cylindrical central electrode, $r_C$. $R_{loop}$ is then calculated from equation (20) as:

$$R_{loop} = \sum_{k=1 \to n} R_k \qquad (20)$$

Equation (10) can now be used to compute the current. During the initial steps, one can compute amounts of each of the analytes and OH⁻ in each of the zones $A_{i,k}$ and $A_{OH,k}$ as follows:

$$A_{i,k} = C_{i,k} V_k \qquad (21a)$$

$$A_{OH,k} = C_{OH,k} V_k \qquad (21b)$$

The equation for OH⁻ and for the analytes will generally be the same, and need not be replicated unless there is a difference. Thus, all equations for analytes for which a corresponding equation exists for OH⁻ will be designated by 'a' after the numeric reference, which will indicate an identical corresponding equation 'b', not set forth herein, that applies to hydroxide. The following method steps are then carried out:

6. The amount of analyte i transferred from zone k to zone k−1, $\Delta i A_{i,k}$ over an iteration period $\Delta t$ is calculated essentially per equation (14):

$$\Delta A_{i,k} = I \rho_k \mu C_{i,k} \Delta t \qquad (22a)$$

7. The new amounts in each zone are then calculated:

$$A_{i,k}(\text{new}) = A_{i,k}(\text{old}) - \Delta A_{i,k} + \Delta A_{i,k+1} \qquad (23a)$$

For all the analytes, at outermost zone n, $\Delta A_{i,K+1}$ is taken to be zero. However, hydroxide is generated at this zone and thus:

$$\Delta A_{OH,n+1} = I \Delta t / F \qquad (24)$$

8. The amount $\Delta A_{i,1}$ the amount of analyte introduced into the capillary, a cumulative tally of which is kept.
9. For each zone k, the value of $\rho_k$ is computed according to equation 17 and the current I is computed using equations 19, 20, and 10.
10. Method steps 6, 7, 8, and 9 are repeated until the desired EI period has been reached.

Figure 5:
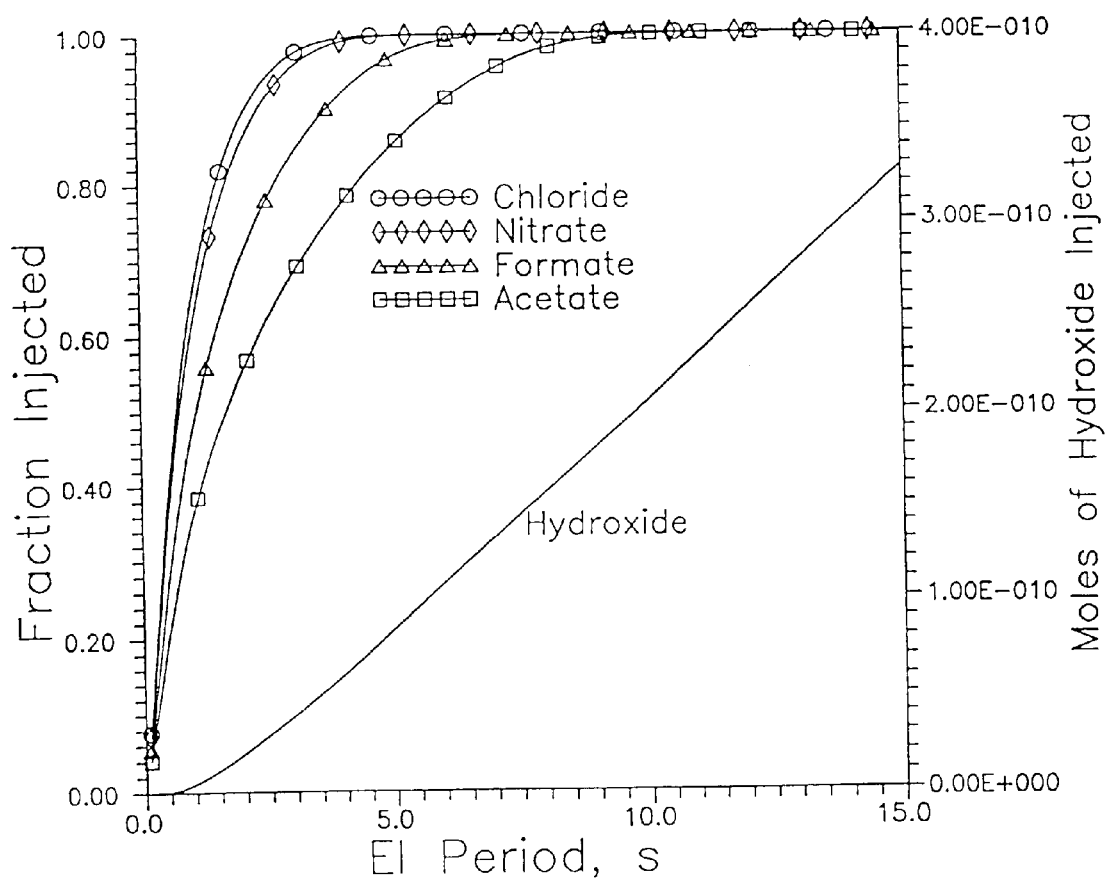
FIG. 5 depicts numerical simulation of EI from a film in which no mixing is present, other conditions being the same as for FIG. 4, according to the present invention.
Figure 6:
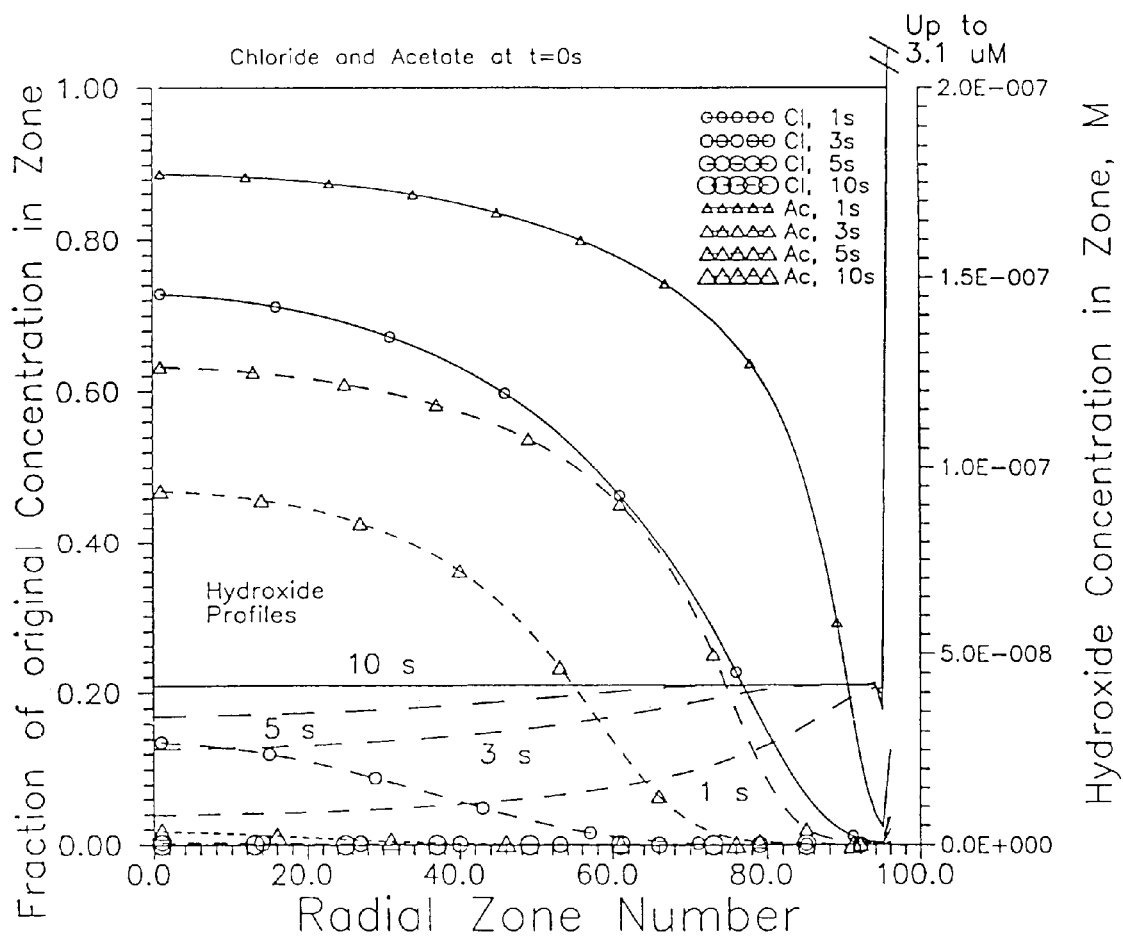
FIG. 6 depicts spatial distribution of chloride, acetate and hydroxide in a film as a function of EI period, other conditions being the same as for FIG. 5, according to the present invention.

FIG. 5 depicts an EI simulation using the above approach, in which a model predicted quantitative injection of chloride in 5 s, and predicted even acetate within 10 s. FIG. 6 depicts radial analyte distributions as a function of EI times. Note in FIG. 6 the radial distribution of the analytes as EI time progresses. Both chloride and acetate are depleted from the outer zones first, and then attain virtual plateaus as they approach the center of the loop (or other finite microreservoir-electrode). The chloride disappears much faster than the slower moving acetate. OH⁻ is generated at the outer electrode and has a distribution that at any time exhibits a concentration that increases almost exponentially as the outer zone is approached. This increase increases with increasing EI period, and is essentially the opposite behavior of the analyte ions. The residual concentration of the analytes in the outermost zone is artificially high, as described herein.

Applicants' model attempts to account for diffusion. At first glance, it may seem that liquid phase diffusion is slow and may be neglected relative to electric field-governed transport of ions. While this may be true during EI initial stages, diffusive transport has two important effects when dealing with nearly exhaustive analyte introduction. First, diffusive mixing may oppose unidirectional electromigration governed transport, and thereby prolong the time necessary to introduce any analyte in a near quantitative fashion. Second, during the latter portion of an EI period in the outermost zone, NaOh concentration becomes sufficiently high that the zone is very conductive, and the local electric field is low. In this case, diffusion will greatly aid transport, especially for OH⁻, inward from the outermost zone. One may assume Fickian diffusive transport between two neighboring segments such that the amount of species i transported by diffusion from segment k to segment k−1, $\Delta A D_{i,k}$ is given by:

$$\Delta A_{Di,k} = D_i (C_{i,k} - C_{i,k-1}) a / \Delta r \qquad (25a)$$

Where $D_i$ is the diffusion coefficient (also equal to $\mu_i RT/F$), a is the interfacial area of transport given by $2\pi r_{k-1} h$, and $\Delta r$ is the diffusion distance, the mean radial distance between two adjoining segments, given by $(r_k - r_{k-2})/2$. R is the universal gas constant, and T denotes absolute temperature. The modified form of equation (22), which takes into account diffusive transport is thus given by:

$$\Delta A_{i,k} = \mu \Delta t (I \rho_{ki} C_{i,k} + 4\pi RT r_{k-1} h (C_{i,k} - C_{i,k-1}) / (F(r_k - r_{k-2}))) \qquad (26A)$$

Figure 7:
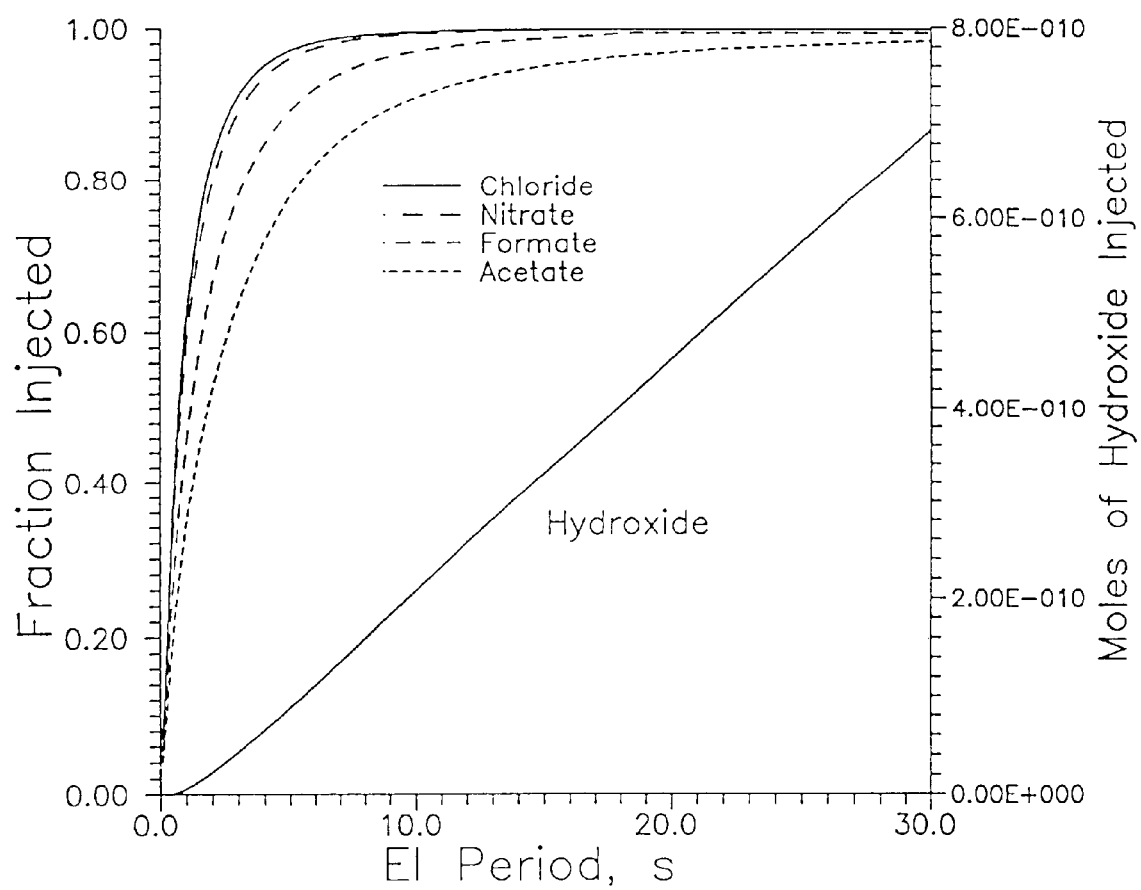
FIG. 7 depicts numerical simulation of EI from a film in which the model includes diffusional mixing, other conditions being the same as for FIG. 5, according to the present invention.
Figure 8:
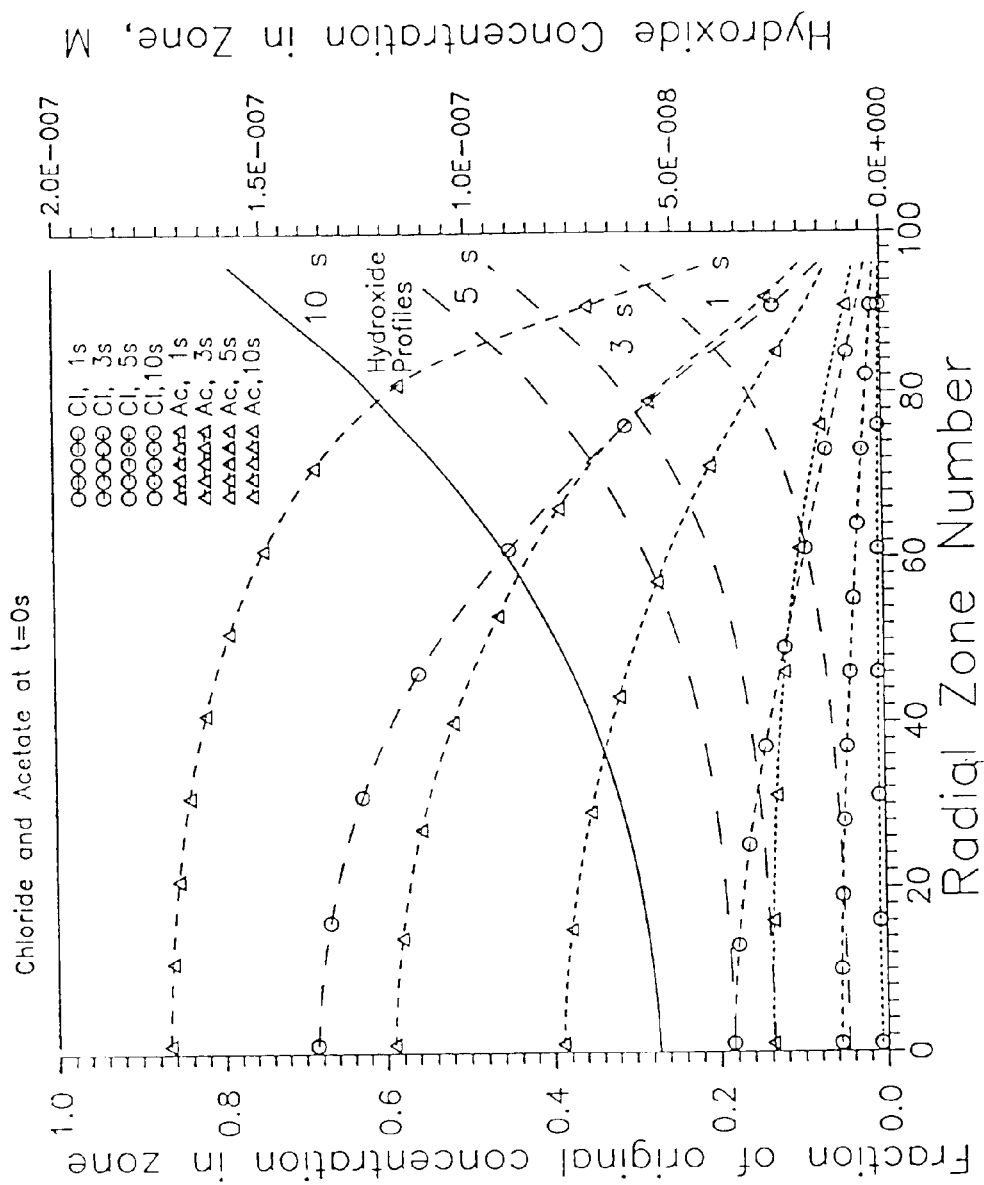
FIG. 8 depicts spatial distribution of chloride, acetate and hydroxide in a film as a function of EI period, in which model includes diffusional mixing, according to the present invention.

Iterative computation is then carried out along the same lines as described earlier herein. FIGS. 7 and 8 depict the outputs corresponding to FIGS. 5 and 6, except that diffusion is now taken into account. Note that consideration of diffusional mixing has a significant effect upon decelerating the rate of analyte introduction through EI. The greater mixing of hydroxide from the outermost zone is also notable. For the same reason, the artifact residual analyte concentrations in the outermost zone is no longer visible. The differences between FIGS. 7 and 8 and counterpart FIGS. 4 and 5 appear to arise solely from diffusion effects. The electrical mobility of an analyte is linearly related to its diffusion coefficient. But while electromigration is an electric field-dependent process, diffusion is not. Consequently, the relative importance of diffusion increases at lower applied EI voltages. The differences between the two sets of results can thus be interpreted in terms of how changes in the applied EI voltage may affect the process. Consider the effect of changing applied voltage in a numerical model. In contrast to equation (1), at a constant voltage time product, EI is more efficient at higher applied voltages. For example, for acetate 94.59% vs. 91.33% is introduced with 5 s at −6 kV, vs. 10 s at −3 kV, and 99.87% vs. 99.62% is introduced with 5 s at 18 kV vs. 10 s at 9 kV.

Applicants have also attempted to account for effects from non-diffusional mixing and electroosmotic flow. Admittedly, assuming that the entire film is one well mixed pot is an oversimplification. However, assuming that the only mixing process is diffusion can also be inaccurate.

Applicants' iterative computational procedure assumes that the contents of every 10 $\mu$m thick segment is homogenized every 100 $\mu$s, which assumption represents a process substantially more efficient than diffusional mixing alone. However, because the computations converge at iteration steps <100 $\mu$s, no error appears to be thus incurred. In an real system, there is reason to believe that more efficient means of mixing exists, particularly in the innermost and outermost zones. In the first case, the presence of the capillary tip may bring about non-diffusional mixing, and in the second case, electrolytic gas evolution may lead to significant mixing.

These phenomena can be accounted for by a choice of radial distances that define the innermost and outermost zones because such selection effectively changes the volume that is homogenized at each iteration step. In applicants' model, varying RINZONE between 50 µm and 150 µm (while the outermost zone width and the loop radius are maintained constant at 10 µm and 1000 µm, respectively) had very little effect on the results. The fraction of chloride injected in 10 s decreases from 99.4790% to 99.4786% with the stated increase in RINZONE, and the change for acetate is also very small, from 91.1068% to 91.1009%.

The effect of changing the width of the outermost zone is more pronounced. In this case, the fraction injected of all ions decreases as zone width is increased. RINZONE and the loop radius were maintained constant at 50 µm and 1000 µm, respectively, for the outermost zonewidth of 10, 50, 100, 200 and 350 µm. The fractions of chloride injected in 10 s were respectively 99.48%, 99.40%, 99.04%, 97.56%, and 94.40%, and the fractions of acetate were 91.11%, 90.82%, 89.72%, 86.01%, and 79.52%. The greater effect of changing the width of the outermost zone is understandable. NaOH is produced in this region and there can be large changes in the effective electric field, which can affect a greater volume if the changes occur over a larger volume.

Electroosmotic flow, $Q_{eo}$, during EI in the present system is quite small, 0.500 nL/s. To account for electroosmotic flow, it is assumed that the amount introduced by EOF within any given iteration period corresponds to the same composition as in the innermost zone. The modified form of Step 8 (immediately after equation (24)) is thus formulated:

$$m_{i,inj}(\text{new}) = m_{i,inj}(\text{old}) + \Delta A_{i,k} + Q_{eo}\Delta t C_{t,1} \quad (27)$$

where $m_{i,inj}$ is the amount of analyte i injected into the capillary and $\Delta A_{i,k}$ is given by equation (26). The volume change in the film due to EOF can be accounted for by a corresponding change in the film thickness h. However, this is somewhat a cosmetic step as vertical transport is not regarded as a limiting factor.

More importantly, it is necessary to account for changes in amount of analyte in the film and for concentration changes. For want of a more accurate alternative in depicting the real system, it is assumed that the analyte that is injected into the capillary is reflected by a change in analyte concentration throughout the film, in a manner proportional to the analyte concentration in each zone:

$$C_{i,k}(\text{new}) = C_{i,k}(\text{old}) \cdot (m_{i,rem} - Q_{eo}\Delta t C_{i,1}/m_{i,rem} \cdot (h/(h-\Delta h)) \quad (28)$$

where mi,rem is the residual amount of analyte i in the film, and Δh is given by:

$$\Delta h = Q_{eo}\Delta t/(\pi r_{out}^2) \quad (30)$$

where h is the current thickness of the film. Note that on the right hand side of equation (28) the first term accounts for change in the amount, while the second term accounts for change in volume by changing the thickness of the film.

In applicants' experimental system, EOF was very slow and $Q_{eo}$ accounts for only 1.5% of the film volume over a 30 s EI period at 3 kV. As such, this refinement of applicants' model leads to hardly any noticeable change, e.g., for a 10 s EI period with acetate, the fraction introduced increases from 91.11% to 91.33%. However, a greater change is observed at higher EOF, e.g., using the same example as above, the fraction introduced was 93.42% when the EOF was tenfold greater.

As noted, it is desired to maintain a finite, small microreservoir, preferably less than about 1 µL in volume. Applicants' wire loop, as depicted in FIGS. 3A, 3B, advantageously provide such a microreservoir. Further, such a microreservoir also provides the ability to subject the entire sample within to a uniform electric field, by using the microreservoir metal loop as a high voltage electrode. Other microreservoir configurations have been examined by applicants, e.g., a conductive hemisphere such as was described with respect to FIG. 3C.

Figure 9:
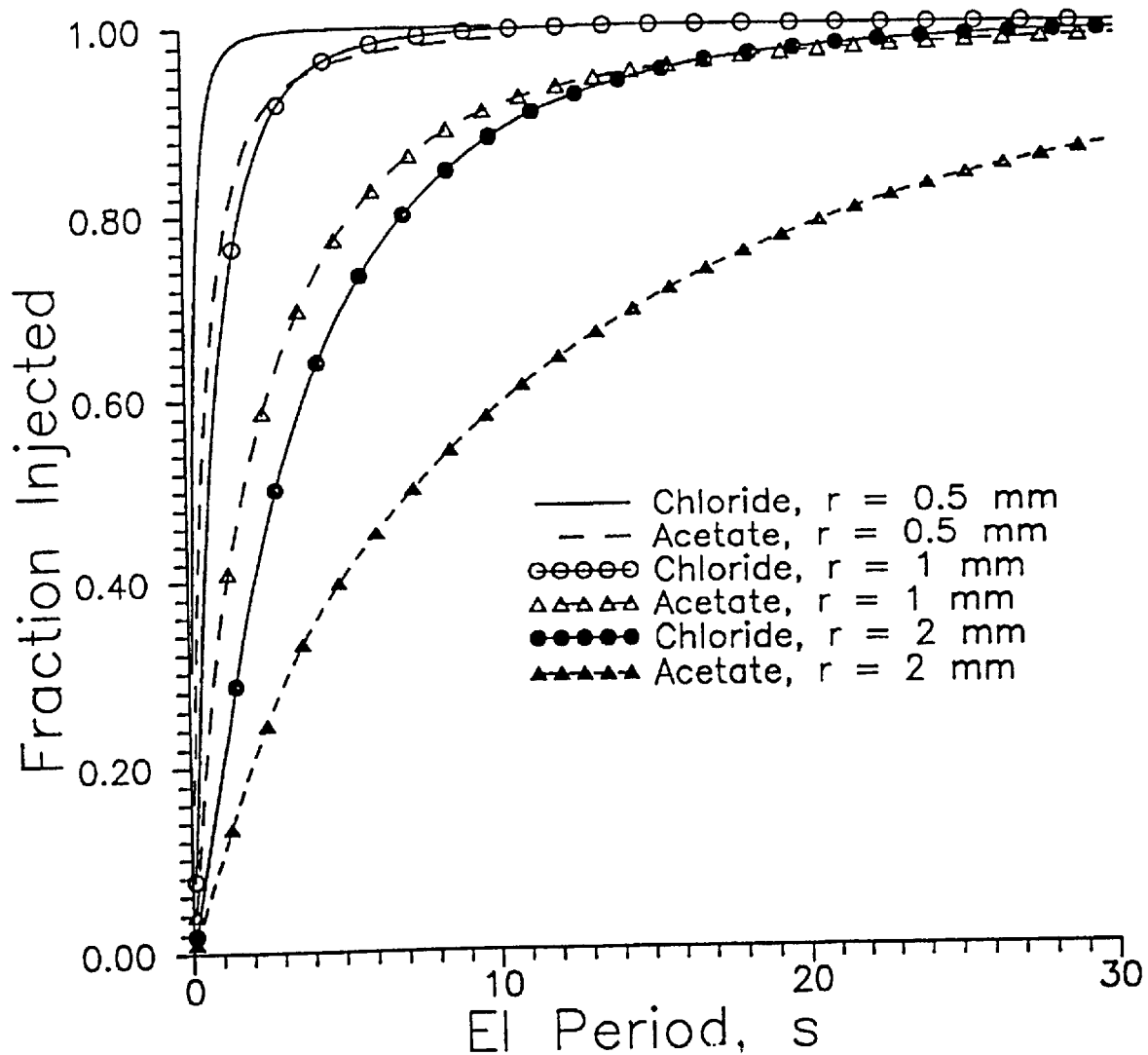
FIG. 9 depicts fraction of chloride and acetate injected as a function of loop radius and EI period, according to the present invention.

Consider the effects of the radius dimension of a wire loop or a hemispheric microreservoir. Understandably, the sample volume effectively changes when the radius is changed. For a given applied voltage, a considerably longer time period is required for "exhaustive" EI. FIG. 9 depicts the results of a numerical simulation for fractions of chloride and acetate injected as a function of microreservoir loop radius and EI period.

For reference purposes, applicants performed and examined conventional hydrodynamic and conventional EI injection from a vial, using the same system and loop-electrode as has been described herein. Hydrodynamic injection was linear with time, e.g., for 10 s to 90 s, the height difference was 4.7 cm, using N,N-dimethylformamide as sample.

The peak area in arbitrary units is given by equation (27) as follows:

peak area(arb. units)=12.39±0.37t(sec)−(19.66±3.78);

$$r^2 = 0.9867 \quad (27)$$

Conventional EI was carried out from a vial with a Cl⁻, NO₃⁻, HCOO⁻, CH₃COO⁻ trace standard mixture. For an EI period of 1 s to 30 s with a HV of −3 kV, all of the individual ions were introduced at a rate linearly proportional to the EI period. Individual $r^2$ values were 0.9976 (Cl⁻), 0.9980 (NO₃⁻), 0.9968 (HCOO⁻), and 0.9904 (CH₃COO⁻). Neither the concentration of the individual analytes in the sample, nor their response factors were the same. Thus, it is convenient to express the results in terms of the equivalent volumetric sample introduction rate. This rate varies with the mobility of the sample ion, being 0.489±0.008 µL/s (Cl⁻), 0.443±0.007 µL/s (NO₃⁻), 0.338±0.007 µL/s (HCOO⁻), and 0.2373±0.008 µL/s (CH₃COO⁻) µL/s.

The relation of the injection rate $dV_{inj}/dt$ with ionic mobility $\mu_i$ is given by equation (28) as:

$$(dV_{inj}/dt) = (6.69 \pm 0.24) \cdot 102 \,\mu_i - (4.51 \pm 1.54) \cdot 10^{-2},$$

$$r^2 = 0.9975 \quad (28)$$

The above result is in close agreement with what equation (1) would predict. However, these results may be the best that can be expected from such systems, and marked variations from the behavior expected from equation (1) are observable at higher applied voltages.

Applicants conducted experiments at applied EI voltages of −6 kV and up to 15 s, and −9 kV and up to 10 s, in addition to the above described −3 kV measurements. At each applied voltage, the relationship between the sample amount introduced and the EI period was linear for Cl⁻ and NO₃ ($r^2$>0.9970). However, for HCOO⁻ the $r^2$ value was 0.9829 at −9 kV, and for CH₃COO the linear $r^2$ value degraded to 0.96 at −6 kV and to 0.25 at −9 kV.

More significantly, based upon equation (1), one would expect that sample introduction rates would be linearly proportional to the applied voltages. For Cl⁻ and NO₃⁻, the ratio of the introduction rates at −3 kV, −6 kV, and −9 kV were 1:1.59:1.72 and 1:1.45:1.50, respectively, instead of the expected result 1:2:3. Indeed, the introduction rate of nitrate hardly varied between −6 kV and −9 kV. For formate, the observed ratio as a function of the applied voltage was 1:1.25:0.98 and the introduction rate actually decreased at −9 kV. This effect was more pronounced for acetate, with an observed ratio of 1:0.83:0.05. At the highest applied voltage, very little acetate was introduced at all, and the amount had very little dependence on the EI period (viz., low $r^2$ cited above).

It is unlikely that electrochemical reduction of acetate is a plausible mechanism to account for this behavior. Applicants instead presume that this reduction originates in depletion near the capillary tip of the slow moving ions. If so, decreasing the concentration of the analytes would worsen the situation, especially for the more susceptible ions.

Figures 10A, 10B:
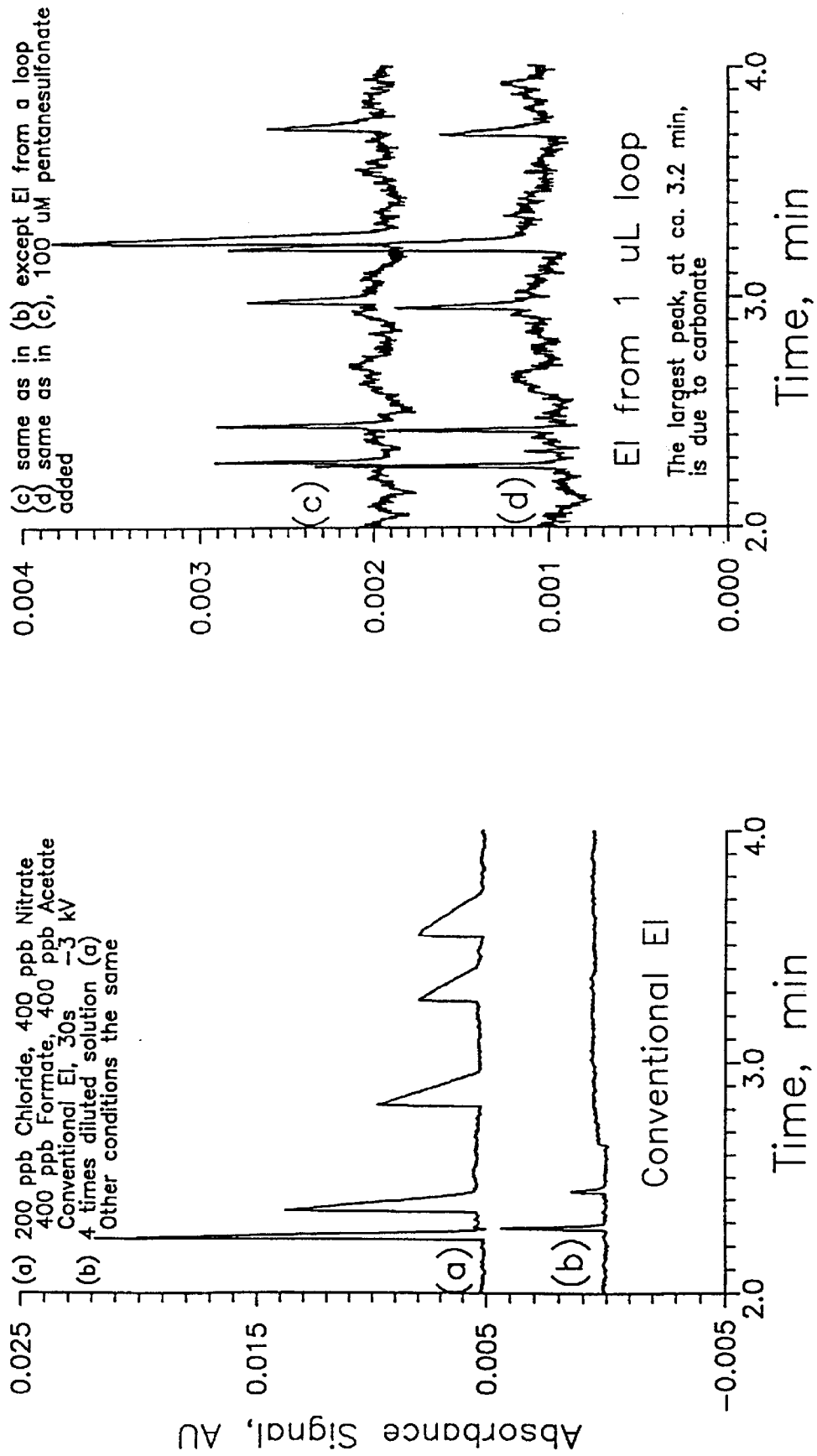
FIGS. 10A and 10B depict, respectively, conventional EI and EI from a loop, according to the present invention.

FIGS. 10A and 10B depict superimposed electropherograms of applicants' trace test standard mixture (FIG. 10A-(*a*)), and the solution of FIG. 10A-(*a*), but diluted four times (FIG. 10A-(*b*)), both solutions subjected to EI for 30 s at −3 kV. Note that formate and acetate are not even discernible in the pherogram of FIG. 10A-(*b*).

In general, such behavior is at least qualitatively understandable. When a capillary and a HV electrode are dipped into a sample vial and EI is attempted, the electric field is present primarily between the capillary tip and the electrode. Thus, effectively only a small part of the sample volume is subjected to the electric field. As EI progresses, the electrolytic production of acid or base further concentrates the electrical field to the same region due to increasing conductance.

In a loop, the hypothetical successive radial zones are electrically effectively in series with each other. But in conventional EI, the various pathways between the capillary tip and the electrode are effectively in parallel, not in series. The major mechanism of replenishment of the analyte ions in this primary field region is diffusion. For an ion of small diffusion coefficient, little transfer occurs. As a result, no concentration gradient develops within the bulk solution, which further inhibits diffusive transport, a self-perpetuating effect. Obviously, the bias will increase if the analyte concentration is low to start with, or if the applied electric field is high.

Consider now electromigration injection (EI) from a symmetrical microreservoir-electrode, such as applicants' loop, and the role of mobility-based bias. An especially important aspect of EI from a loop is that the type of bias depicts in FIG. 10A-(*a*) and FIG. 10A-(*b*) is neither theoretically expected, nor experimentally observed. FIG. 10B-(*c*) depicts the same conditions as in FIG. 10A-(*b*), except that EI is now performed (at the same voltage for the same period) from a loop of 1 μL volume. Not only are all the four expected peaks observed, but a peak due to carbonate is also observed.

A terminating electrolyte such as sodium pentanesulfonate is often added in conventional EI to improve trace analysis, and this was done for the data of FIG. 10B-(*d*). It is apparent from FIG. 10B that nothing is gained in EI from a loop from the addition of such electrolyte. Theory suggests that such bias encountered in conventional EI will be associated with the geometry of the field. Accordingly, applicants conducted an experiment in which the sample was contained in a hemispherical depression of about 10 μL volume in a metal block that also functioned as the HV electrode (see FIG. 3C). The capillary tip was located at the center of this depression. The results are quite similar to that obtained with the loop, underscoring the importance of the geometry of the field experienced by the sample.

Figures 11A, 11B:
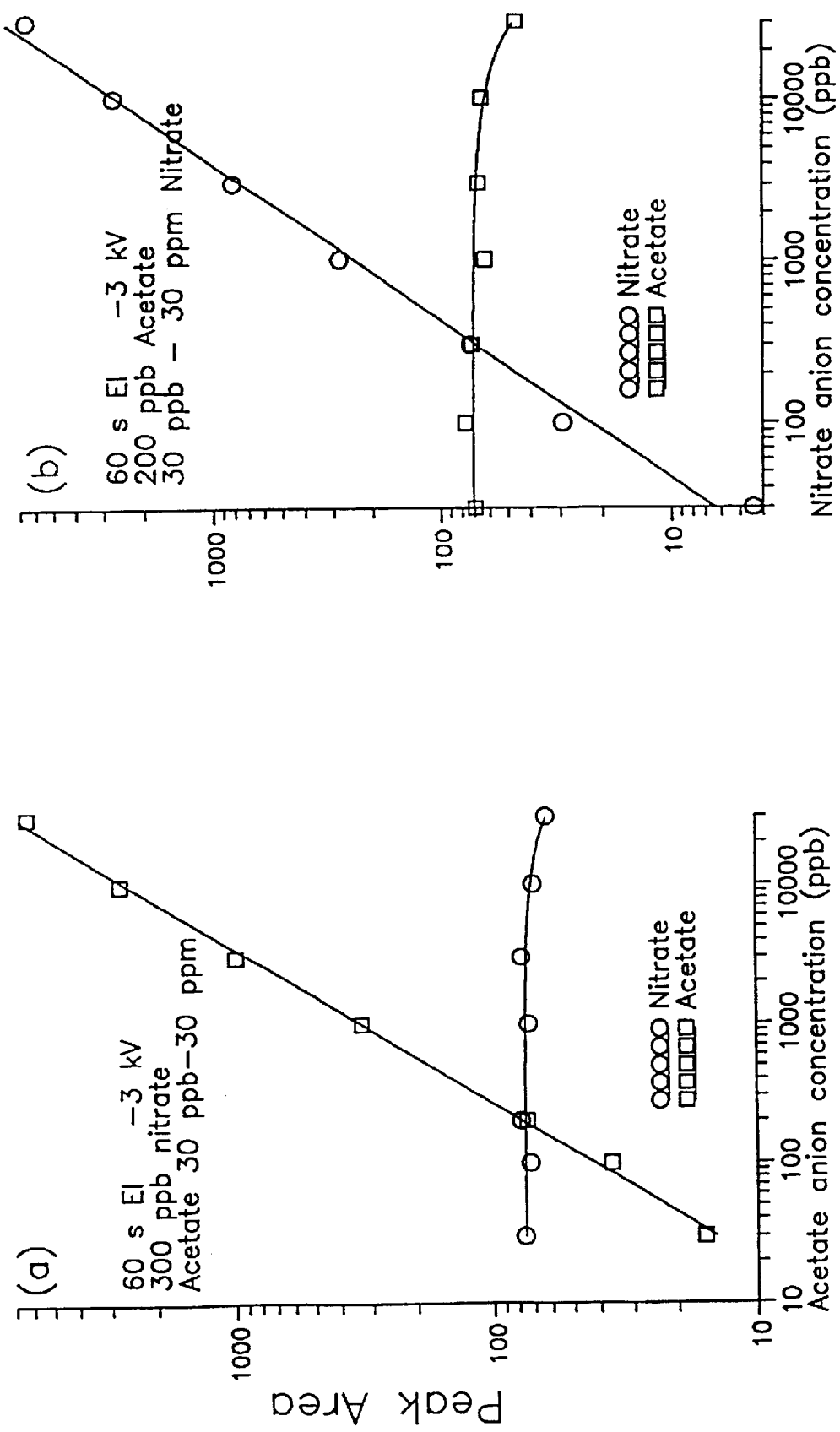
FIG. 11A depicts EI from a small loop exhibiting an extremely large dynamic range with variation of acetate over three orders of magnitude at constant nitrate concentration, according to the present invention.
FIG. 11B depicts variation of nitrate over 3 orders of magnitude at constant acetate concentration, according to the present invention.

FIGS. 11A and 11B depict an even more striking example of the dynamic range of EI from a loop. In FIG. 11A, acetate was varied between 30 ppb to 30 ppm while nitrate was held constant at 300 ppb. For the data in FIG. 11B, acetate was held constant at 200 ppb and nitrate was similarly varied. The peak areas, corrected for migration time shift, demonstrate that the technique disclosed herein by applicants advantageously provides substantially greater dynamic range than is possible with conventional EI.

The results of sample introduction by EI from a loop were investigated at applied voltages ranging from 3 kV to 18 kV, varied in 3 kV steps, for V·t products ranging from 9 kV·s to 108 kV·s. The loop-EI results are quite different from vial-EI, as described earlier herein. For a given V·t product, introduction is more complete at higher applied voltage, as theory predicts.

Figure 12:
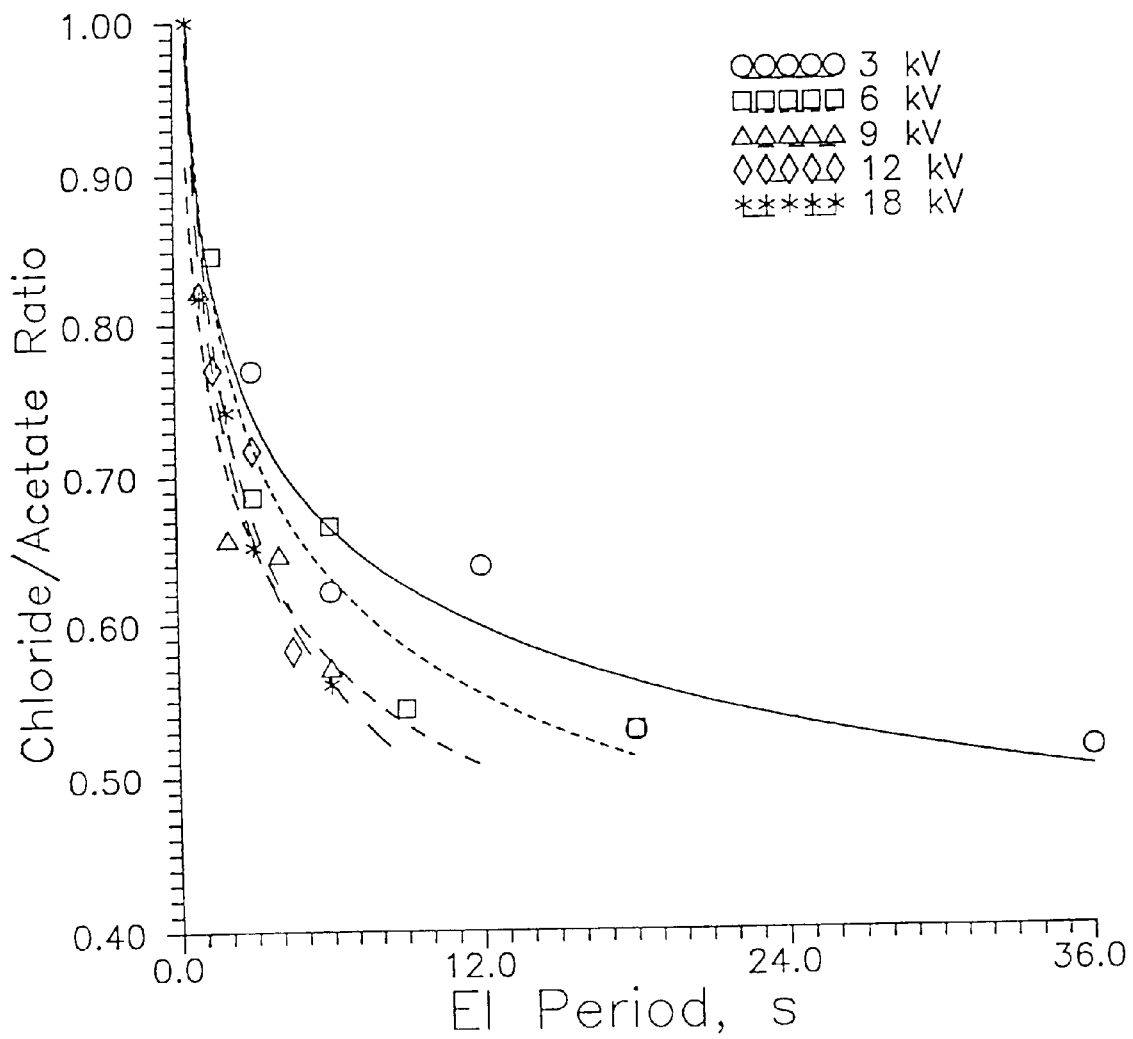
FIG. 12 depicts loop-EI normalized data-for chloride to acetate peak area ratio as a function of HV and EI period, according to the present invention.

FIG. 12 depicts change in chloride/acetate peak area ratio as a function of the EI period at different applied voltages for a 1 μL loop. For this plot, the area ratio when the highest voltage (18 kV) has been applied for the smallest period of time (0.5 s), has been arbitrarily assigned the value of unity. While the bias would be the greatest under these conditions, it is expected to approach the limiting value of 0.535 (acetate/chloride mobility ratio) at higher V·t products. Indeed, this is observed.

Figures 13A, 13B:
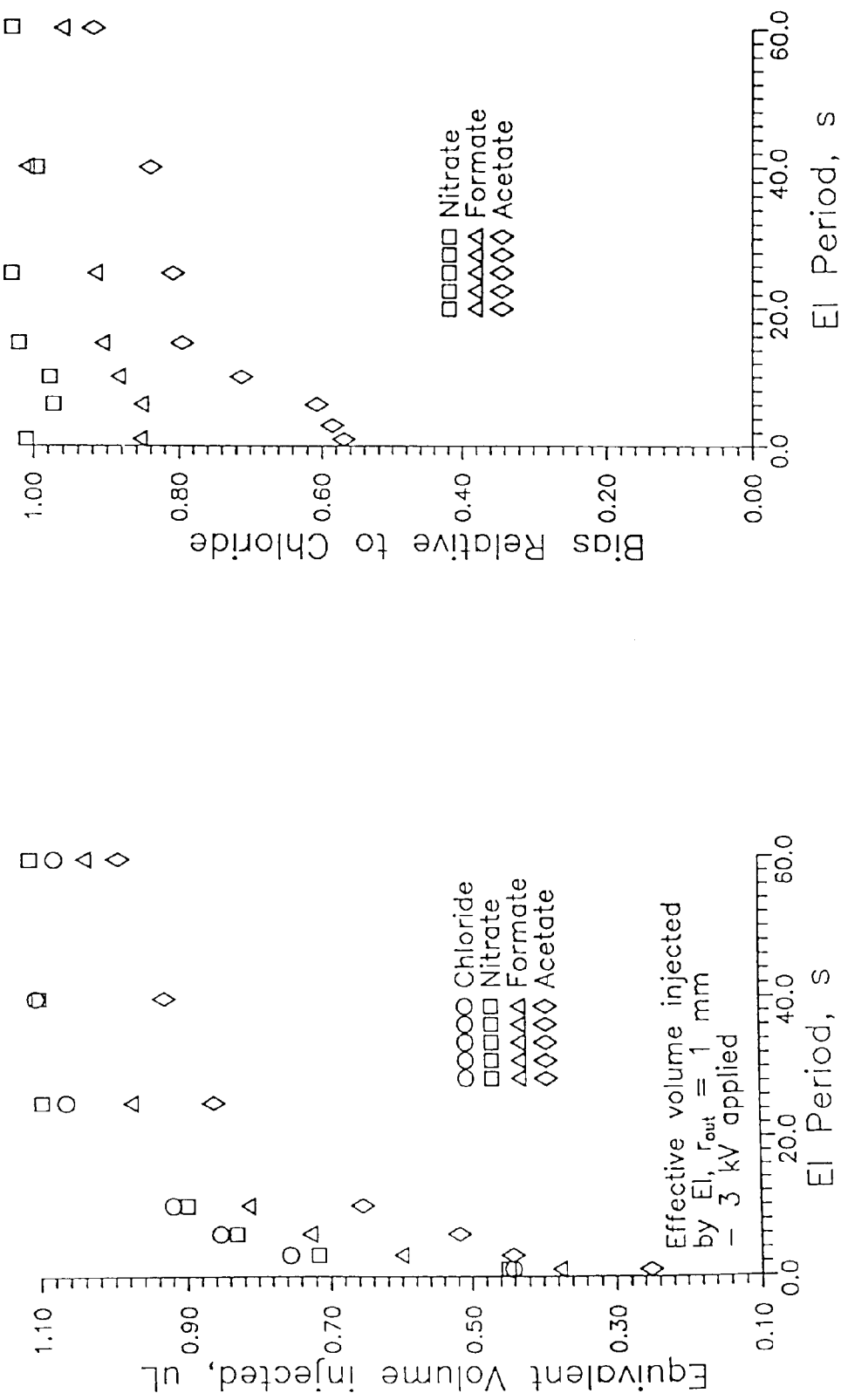
FIG. 13A depicts loop-EI equivalent volume injected as a function of EI, according to the present invention.
FIG. 13B depicts loop-EI bias relative to chloride as a function of EI, according to the present invention.

The completeness of injection and amount of bias was investigated. FIGS. 13A and 13B depict data from an approximately 1 μL volume inclined loop of about 1 mm radius (see FIG. 3B). Because the exact volume was difficult to determine, FIG. 13 uses an ordinate of equivalent volume injected, i.e., analyte contained within that volume. The results are qualitatively similar to the model calculations described in association with presented in FIG. 5. However efficiency was less, in that about 50 s time was required to accomplish what required 10 s in the earlier model. Applicants believe this is a consequence of the fact that the present model does not take into account limitations in vertical transport, e.g., a 320 μm thick film is hardly infinitesimally thin. However the broad general pattern is the same as that in the model. FIG. 13B depicts that with exhaustive electromigration, bias is greatly diminished, although it is not completely eliminated.

Figure 14:
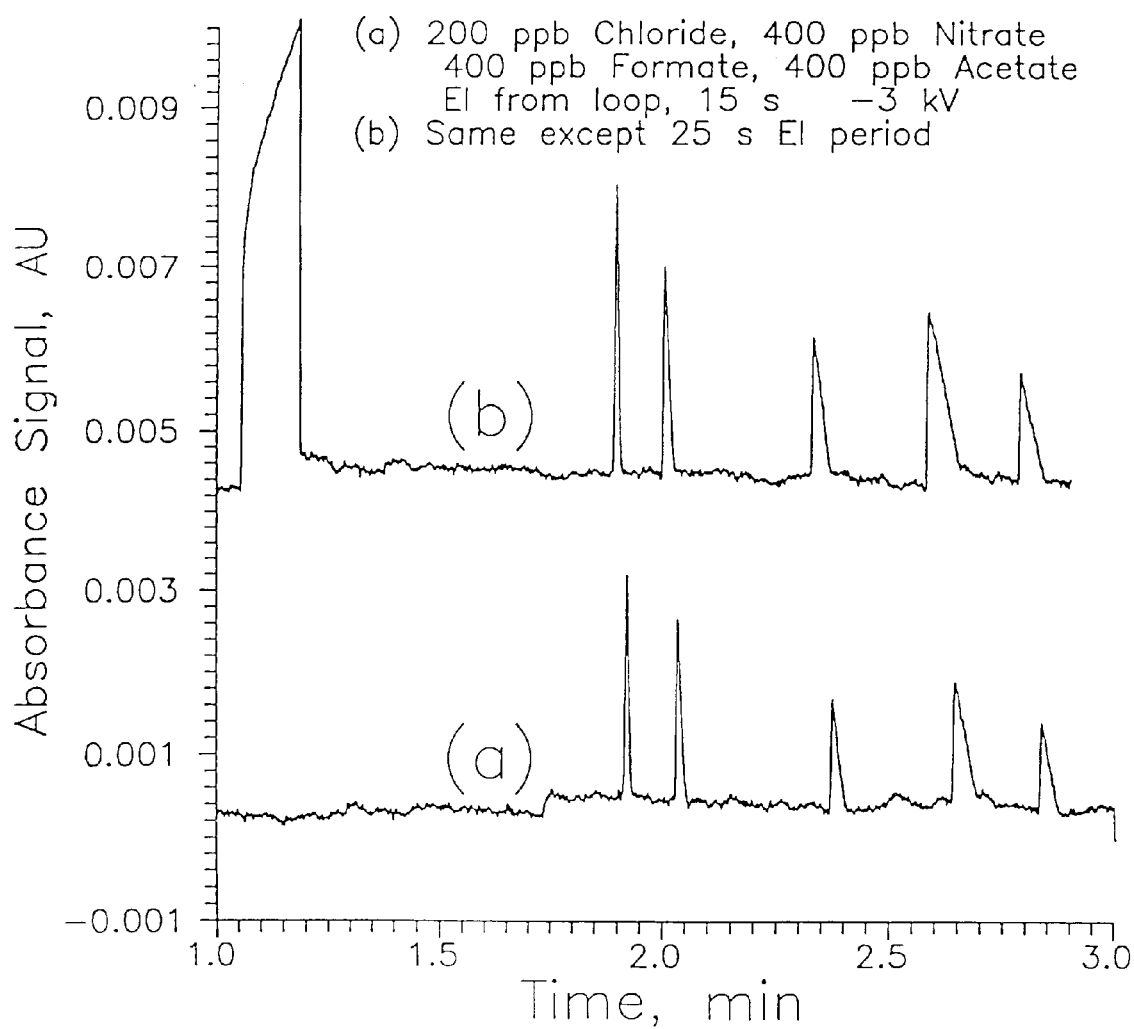
FIG. 14 depicts hydroxide introduction upon prolonged EI from a loop, according to the present invention.

As may be theoretically expected, applicants have observed that larger loops lead to less complete injection and greater bias when EI is conducted for the same period at the same voltage. On the other hand, because vertical planar loops hold less liquid, injection is more complete and bias is less with these loops under the same EI conditions for the same loop radius. Since hydroxide is formed as the result of EI, it is injected into the system. The BGE has a finite buffer capacity and the OH− peak thus appears only after this capacity is exceeded. An example is shown in FIG. 14, in which no hydroxide peak is visible for a 15 s EI period, but is by far the major peak by an EI period of 25 s. The integrated hydroxide peak area for EI periods ranging from 25 s to 60 s is correlated linearly with the EI period with an $r^2$ value of 0.9996. A linear relationship of OH− introduction with time was seen in FIG. 4. It is also predictable that a positive peak due to hydroxide first occurs after 20 s of EI.

In summary, applicants have demonstrated that substantial improvements in EI in CE can result if injection is made from a small finite volume in which the entire sample is exposed to the electrical field, preferably symmetrically. Indeed, the use of microreservoir-electrodes disclosed herein may constitute a more convenient and powerful injection method in CE than what is presently practiced in the prior art. Understandably, applicants' results using films formed on wire loops may be applied to other geometries as well, in addition to forming hemispherical wells in a microtiter metallized plate. An autosampler configuration may be used with a variety of microreservoir-electrodes.

Applicants anticipate that the present invention can not only improve sampling and injection in CE and other separation systems, but will simultaneously improve detection limits beyond what is presently available with conventional detectors. Introduction of $H^+$ or $OH^-$ presumably can be prevented using membrane arrangements, should such introduction become a significant factor. Modifications and variations may be made to the disclosed embodiments without departing from the subject and spirit of the invention as defined by the following claims. For example, although the present invention has been described primarily with respect to tests made using a capillary electrophoresis separation system, the present invention may also be practiced in a capillary electrochromatography separation system.

What is claimed is:

1. In a capillary separation system in which analyte ions of a chosen polarity in a sample are caused to migrate through a separation capillary by application of high voltage, a method of exhaustively injecting said analyte ions by electromigration into said capillary such that injection is substantially independent of ionic mobility of individual ones of said analyte ions and is substantially independent of sample conductivity, the method comprising the following steps:

(a) providing an electrically conductive symmetrically-shaped microreservoir fabricated from a conductive wire formed into a circular loop to define a desired loop area that defines a substantially constant finite holding volume in which a reproducible volume of said sample is retained;

(b) disposing an entry tip of said separation capillary in contact with a portion of said sample in said microreservoir; and (c) subjecting said sample in said microreservoir to a radially symmetric electric field by coupling one lead of said high voltage to said microreservoir and energizing said high voltage for a time period causing ions in said sample of said chosen polarity to be substantially exhaustively introduced into said tip of said separation capillary.

2. The method of claim 1, wherein said system is an electrophoretic separation system.

3. The method of claim 1, wherein said system is a capillary electrochromatographic separation system.

4. The method of claim 1, wherein step (a) includes fabricating said microreservoir with a loop plane oriented in a plane parallel to a longitudinal axis of said separation capillary.

5. The method of claim 1, wherein step (a) includes fabricating said microreservoir with a loop plane offset from a longitudinal axis of said separation capillary by an angle ranging from about 45° to about 90°.

6. The method of claim 1, wherein said microreservoir defines a holding volume that is symmetrically shaped.

7. The method of claim 1, wherein step (b) includes disposing said entry tip of said separation capillary in contact with a portion of said sample at a symmetrically central portion of said microreservoir.

8. The method of claim 1, wherein at step (a) said holding volume is a volume selected from the group consisting of (a) a volume less than about 2 $\mu L$, (b) a volume less than about 1 $\mu L$, and (c) a volume less than about 0.5 $\mu L$.

9. In a capillary separation system in which analyte ions of a chosen polarity in a sample are caused to migrate through a separation capillary by application of high voltage, a method of exhaustively injecting said analyte ions by electromigration into said capillary such that injection is substantially independent of ionic mobility of individual ones of said analyte ions and is substantially independent of sample conductivity, the method comprising the following steps:

(a) providing an electrically conductive symmetrically-shaped microreservoir that includes a base portion in which there is defined a symmetrical hemisphere cavity having a desired constant finite holding volume in which a reproducible volume of said sample is retained;

(b) disposing an entry tip of said separation capillary in contact with a portion of said sample in said microreservoir; and (c) subjecting said sample in said microreservoir to a radially symmetric electric field by coupling one lead of said high voltage to said microreservoir and energizing said high voltage for a time period causing ions in said sample of said chosen polarity to be substantially exhaustively introduced into said tip of said separation capillary.

10. The method of claim 9, wherein said system is an electrophoretic separation system.

11. The method of claim 9, wherein said system is a capillary electrochromatographic separation system.

12. The method of claim 9, wherein step (b) includes disposing said entry tip of said separation capillary in contact with a portion of said sample at a symmetrically central portion of said microreservoir.

13. The method of claim 9, wherein at step (a) said holding volume is a volume selected from the group consisting of (a) a volume less than about 2 $\mu L$, (b) a volume less than about 1 $\mu L$, and (c) a volume less than about 0.5 $\mu L$.

* * * * *

UNITED STATES PATENT AND TRADEMARK OFFICE
CERTIFICATE OF CORRECTION

PATENT NO.   : 6,086,736
DATED        : July 11, 2000
INVENTOR(S)  : Purnendu K. Dasgupta et al.

It is certified that error appears in the above-identified patent and that said Letters Patent is hereby corrected as shown below:

Column 7,
Line 30, delete the equation (1) and insert therefor:

$$--Q_i = (\mu_i + \mu_{eo})\pi r_c^2 VC_i t/L \quad (1)--$$

Line 31, change "$\mu^i$ and $\mu^{eo}$" to -- $\mu_i$ and $\mu_{eo}$ --.
Line 43, delete the equation (2) and insert therefor:

$$--M_i = dQ_i/dt = (E\mu_i + u_{eo})aC_i \quad (2)--$$

Line 53, after relative to and before equation (2), delete "$E_{fu}$," and insert therefor:

$$--E_{\mu i}, --\ .$$

Column 8,
Line 2, at the beginning of the line delete "$\pi r_c^2$" and insert therefor:

$$--\pi r c^2 --\ .$$

Line 5, after "radius" delete "re" and insert therefor -- $r_e$ --.
Line 8, delete equation (4) and insert therefor:

$$--r_e = rc^2/2h \quad (4)--$$

UNITED STATES PATENT AND TRADEMARK OFFICE
CERTIFICATE OF CORRECTION

PATENT NO. : 6,086,736
DATED : July 11, 2000
INVENTOR(S) : Purnendu K. Dasgupta et al.

It is certified that error appears in the above-identified patent and that said Letters Patent is hereby corrected as shown below:

Column 10,
Line 60, delete equation (18) and insert therefor:

$$-- V_k = \pi(r_k^2 - r_{k-1}^2)h \quad (18) -- .$$

Column 11,
Line 25, delete equation (22a) and insert therefor:

$$-- \Delta A_{i,k} = Ip_k \mu_i C_{i,k} \Delta t \quad (22a) --$$

Signed and Sealed this

Nineteenth Day of November, 2002

*Attest:*

*Attesting Officer*

JAMES E. ROGAN
*Director of the United States Patent and Trademark Office*